(12) United States Patent
Robert et al.

(10) Patent No.: US 8,609,435 B2
(45) Date of Patent: Dec. 17, 2013

(54) ANALYZING AND TYPING MONOCLONAL PROTEINS BY CAPILLARY ELECTROPHORESIS AND IMMUNODISPLACEMENT

(75) Inventors: Frédéric Robert, Mennecy (FR); Régis Andre, Paris (FR)

(73) Assignee: SEBIA (FR)

( * ) Notice: Subject to any disclaimer, the term of this patent is extended or adjusted under 35 U.S.C. 154(b) by 848 days.

(21) Appl. No.: 10/984,252

(22) Filed: Nov. 9, 2004

(65) Prior Publication Data

US 2005/0164302 A1 Jul. 28, 2005

(30) Foreign Application Priority Data

Nov. 12, 2003 (FR) ...................................... 03 13246

(51) Int. Cl.
  *G01N 33/561* (2006.01)
(52) U.S. Cl.
  USPC ......................................................... 436/516
(58) Field of Classification Search
  USPC .............. 435/4, 6, 7.1, 7.93–7.94, 288.1, 0.5, 435/513, 516–8, 287.1–287.2, 288.516; 436/516–518, 527, 535, 538, 541, 86, 436/513; 204/164, 180.1, 182.8, 204/183.2–183.3, 450, 461; 424/133.1; 544/106; 510/418, 421, 416
  See application file for complete search history.

(56) References Cited

U.S. PATENT DOCUMENTS

| | | | | |
|---|---|---|---|---|
| 5,169,764 A | * | 12/1992 | Shooter et al. ............... | 435/69.7 |
| 5,228,960 A | | 7/1993 | Liu et al. | |
| 5,431,793 A | * | 7/1995 | Wang et al. .................. | 204/452 |
| 5,459,272 A | * | 10/1995 | Novotny et al. .............. | 546/168 |
| 5,514,794 A | * | 5/1996 | Barton .......................... | 544/106 |
| 5,567,282 A | | 10/1996 | Wang et al. | |
| 5,741,639 A | * | 4/1998 | Ensing et al. ...................... | 435/6 |
| 5,753,094 A | * | 5/1998 | Alter et al. .................... | 204/451 |
| 5,948,231 A | * | 9/1999 | Fuchs et al. ................... | 204/601 |
| 5,958,202 A | * | 9/1999 | Regnier et al. ................ | 204/451 |
| 5,985,275 A | * | 11/1999 | Neurath et al. ............ | 424/133.1 |
| 6,066,440 A | * | 5/2000 | Araki et al. ................... | 430/354 |
| 6,156,179 A | * | 12/2000 | Binder et al. ................. | 204/461 |
| 6,656,899 B1 | * | 12/2003 | Sadlowski et al. ............ | 510/418 |
| 2002/0162744 A1 | * | 11/2002 | Nouadje et al. ............... | 204/451 |
| 2002/0195341 A1 | * | 12/2002 | Robert .......................... | 204/451 |

FOREIGN PATENT DOCUMENTS

| | | |
|---|---|---|
| EP | 0690988 | 4/2000 |
| WO | 92/15316 | 9/1992 |
| WO | 96/33412 | 10/1996 |

(Continued)

OTHER PUBLICATIONS

Keren, "Detection and characterization of monoclonal components in serum and urine," Clin. Chem., 1998, vol. 44, pp. 1143-1145.*

(Continued)

*Primary Examiner* — N C Yang
*Assistant Examiner* — Richard Moerschell
(74) *Attorney, Agent, or Firm* — Lerner, David, Littenberg, Krumholz & Mentlik, LLP

(57) ABSTRACT

A method for capillary electrophoretic analysis of a biological sample, comprising using negatively surcharged modified antibodies so that they migrate to a zone located outside the migration zone for proteins from the biological sample when they are separated during electrophoresis is disclosed. The antibodies have antigenic specificity for a predetermined target protein.

30 Claims, 35 Drawing Sheets

ELECTROPHORESIS OF SERIC PROTEINS
ANTI IgG DAKO, WINDOW 105-350 SECONDS, 122 SECONDS

ELECTROPHORESIS OF SERIC PROTEINS
MODIFIED ANTI IgG, WINDOW 105-350 SECONDS, 267 SECONDS

(56) References Cited

FOREIGN PATENT DOCUMENTS

| WO | 01/11003 | 2/2001 |
|---|---|---|
| WO | WO-02/057736 | 7/2002 |
| WO | WO-02/057737 | 7/2002 |

OTHER PUBLICATIONS

Keren, "Procedures for the evaluation of monoclonal immunoglobulins," Arch. Pathol. Lab Med., Feb. 1999, vol. 123, pp. 126-132.*

Wang et al., "Suppresion of polyclonal immunoglobulin production by M-proteins shows isotype specificity," Annals Clin. Lab. Sci.; 2001, vol. 31, pp. 274-278.*

Clark et al., "Differential diagnosis of gammopathies by capillary electrophoresis and immunosubstraction: Ananlysis of serum sampels problematic by agarose gel electrophoresis," 19 Electrophoresis (1998) 2479-84.

Paquette & Banks, "Detection of specific antibioties using immunosubtraction and capillary electrophoresis instrumentation," 22 Electrophoresis (2001) 2391-97.

Katzmann et al., "Prospective Study of Serum Protein Capillary Zone Electrophoresis and Immunotyping of Monoclonal Proteins by Immunosubtraction," 110 Am. J. Clin. Pathol. (1998) 503-09.

Legros et al., "Carbohydrate-deficient Transferrin Isoforms Measured by Capillary Zone Electrophoresis for Detection of Alcohol Abuse," 48 Clin. Chem. (2002) 2177-86.

* cited by examiner

ELECTROPHORESIS OF SERIC PROTEINS
ANTI IgG DAKO, WINDOW 105-350 SECONDS, 122 SECONDS

ELECTROPHORESIS OF SERIC PROTEINS
MODIFIED ANTI IgG, WINDOW 105-350 SECONDS, 267 SECONDS

ELECTROPHORESIS
SERUM WITH A LAMBDA AT BETA-2-ELP

ELECTROPHORESIS OF SERIC PROTEINS
ANTI IgG

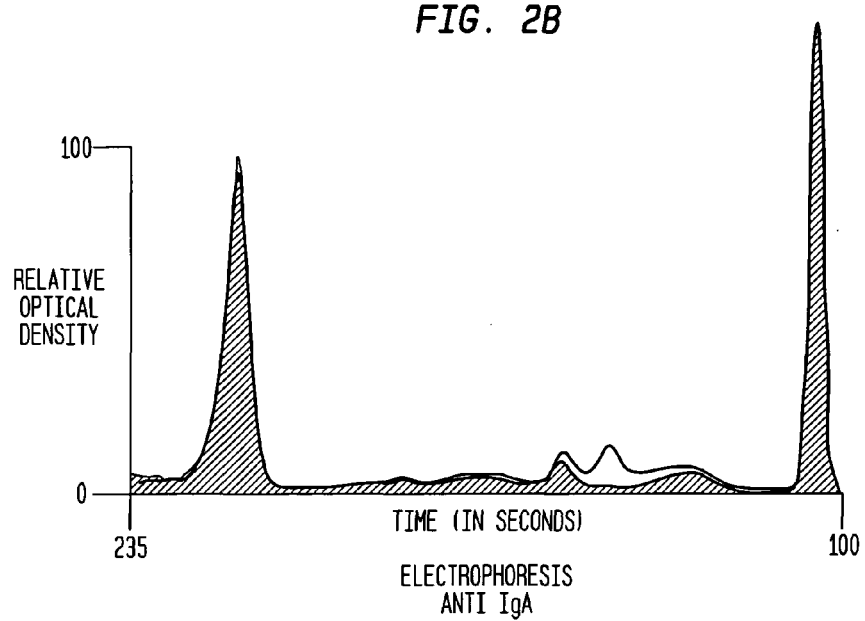
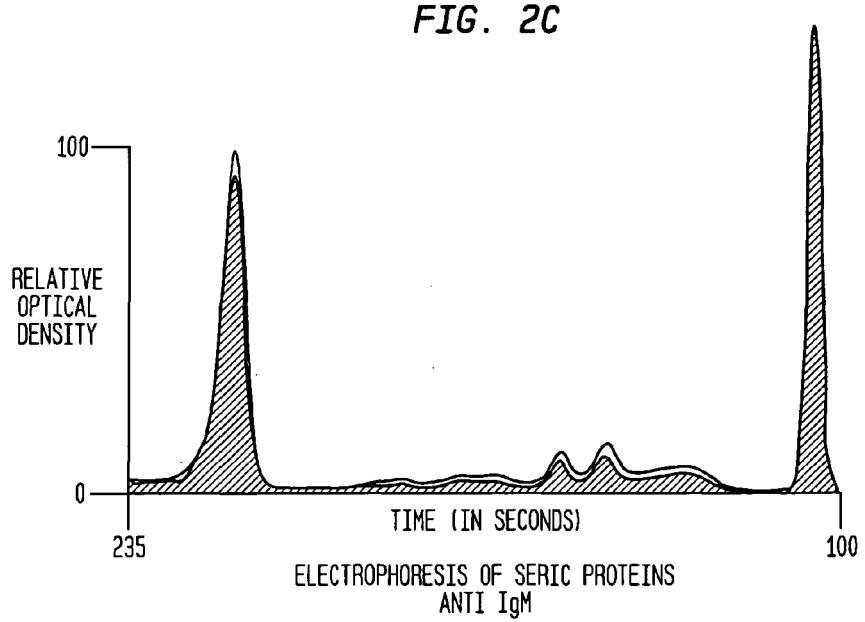

ELECTROPHORESIS OF SERIC PROTEINS
ANTI KAPPA

ELECTROPHORESIS OF SERIC PROTEINS
ANTI LAMBDA

ELECTROPHORESIS OF SERIC PROTEINS
SERUM WITH G LAMBDA AT BETA-1 - ELP

ELECTROPHORESIS OF SERIC PROTEINS
ANTI IgG

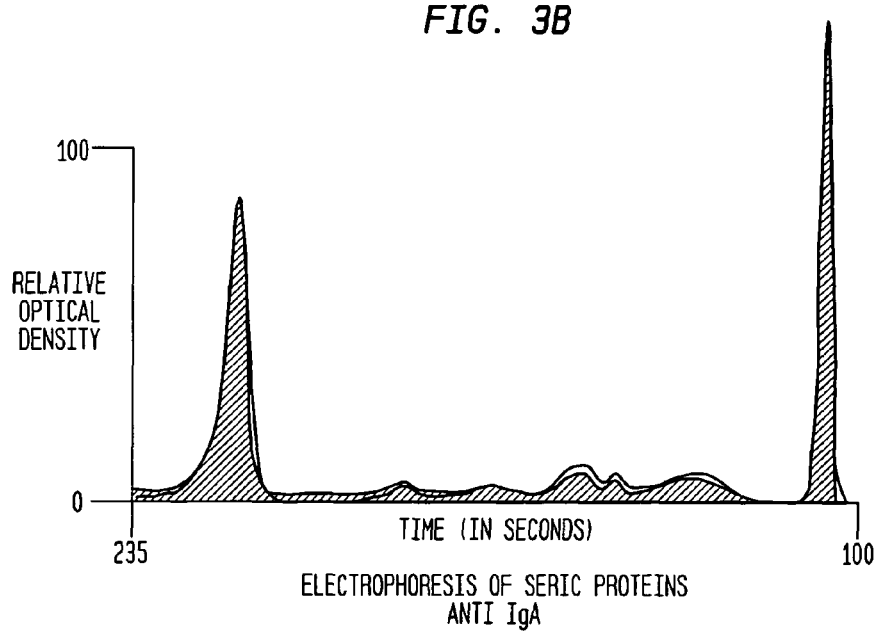
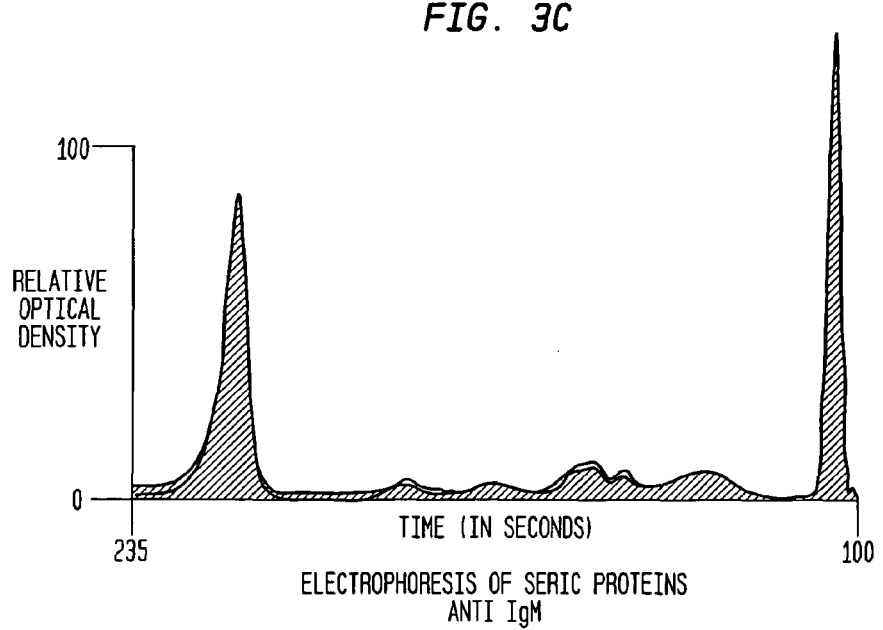

ELECTROPHORESIS OF SERIC PROTEINS
ANTI KAPPA

ELECTROPHORESIS OF SERIC PROTEINS
ANTI LAMBDA

ELECTROPHORESIS
SERUM WITH A KAPPA AT ALPHA-2/BETA-1 - ELP

ELECTROPHORESIS OF SERIC PROTEINS
ANTI IgG

ELECTROPHORESIS OF SERIC PROTEINS
ANTI IgA

ELECTROPHORESIS OF SERIC PROTEINS
ANTI IgM

ELECTROPHORESIS OF SERIC PROTEINS
ANTI KAPPA

ELECTROPHORESIS OF SERIC PROTEINS
ANTI LAMBDA

SERUM WITH G LAMBDA - ELP

ELECTROPHORESIS OF SERIC PROTEINS
ANTI IgG

ELECTROPHORESIS OF SERIC PROTEINS
ANTI IgG

ELECTROPHORESIS OF SERIC PROTEINS
ANTI IgM

ELECTROPHORESIS OF SERIC PROTEINS
ANTI KAPPA

ELECTROPHORESIS OF SERIC PROTEINS
ANTI LAMBDA

ELECTROPHORESIS OF SERIC PROTEINS
SERUM WITH A LAMBDA AT BETA-1/BETA-2 – ELP

ELECTROPHORESIS OF SERIC PROTEINS
ANTI IgG

ELECTROPHORESIS OF SERIC PROTEINS
ANTI KAPPA

ELECTROPHORESIS OF SERIC PROTEINS
ANTI LAMBDA

ELECTROPHORESIS
SERUM WITH M KAPPA - ELP

ELECTROPHORESIS OF SERIC PROTEINS
ANTI IgG

ELECTROPHORESIS OF SERIC PROTEINS
ANTI IgA

ELECTROPHORESIS OF SERIC PROTEINS
ANTI IgM

ELECTROPHORESIS OF SERIC PROTEINS
ANTI KAPPA

ELECTROPHORESIS OF SERIC PROTEINS
ANTI LAMBDA

ELECTROPHORESIS OF SERIC PROTEINS
SERUM WITH FREE LAMBDA AT GAMM - ELP

ELECTROPHORESIS OF SERIC PROTEINS
ANTI IgG

ELECTROPHORESIS OF SERIC PROTEINS
ANTI IgA

ELECTROPHORESIS OF SERIC PROTEINS
ANTI IgM

ELECTROPHORESIS OF SERIC PROTEINS
ANTI KAPPA

ELECTROPHORESIS OF SERIC PROTEINS
ANTI LAMBDA

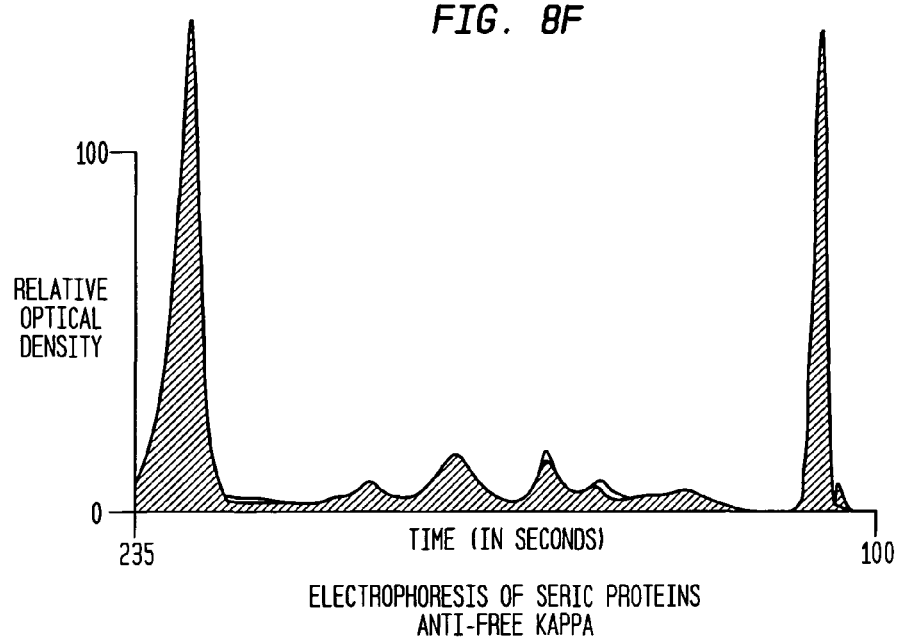
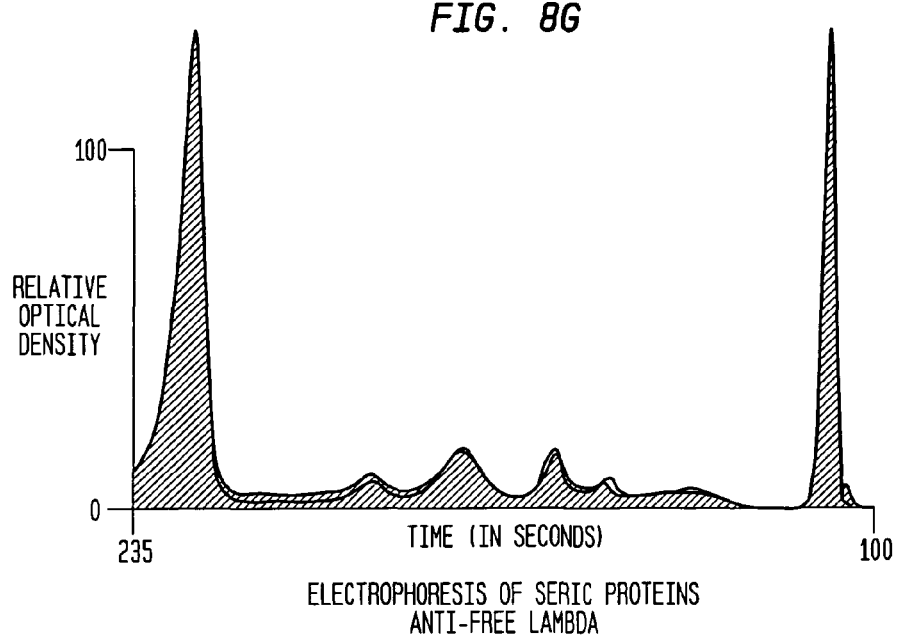

ELECTROPHORESIS OF SERIC PROTEINS
SERUM WITH G LAMBDA AT GAMMA - ELP

ELECTROPHORESIS OF SERIC PROTEINS
ANTI-IgG GRAFTED WITH TRICARBOXYLIC ANHYDRIDE

ELECTROPHORESIS OF SERIC PROTEINS
ANTI IgG GRAFTED WITH MELLITIC ACID

ELECTROPHORESIS OF SERIC PROTEINS
SERUM WITH G KAPPA AT GAMMA, IN-CAPILLARY METHOD - ELP

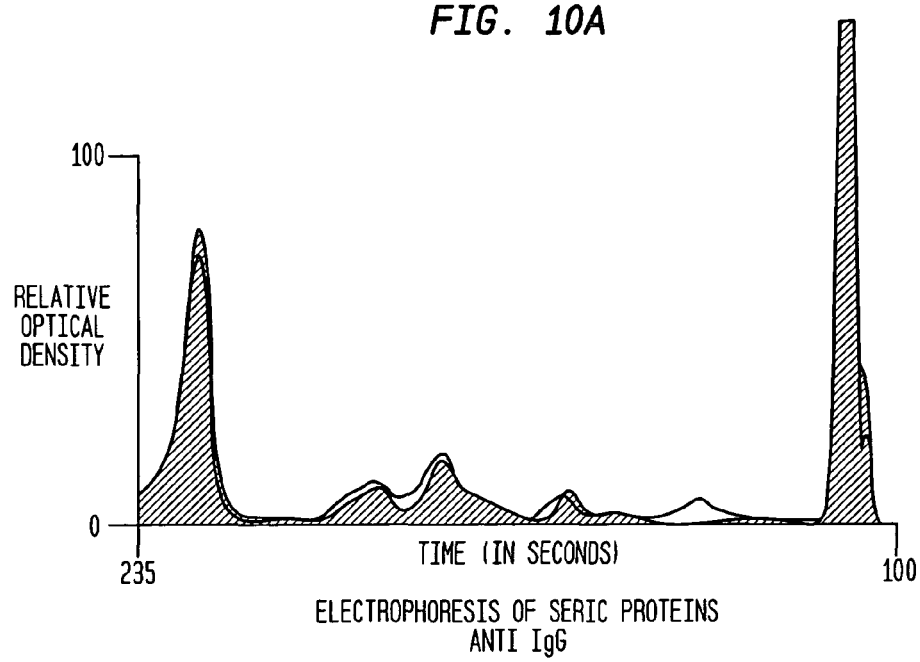
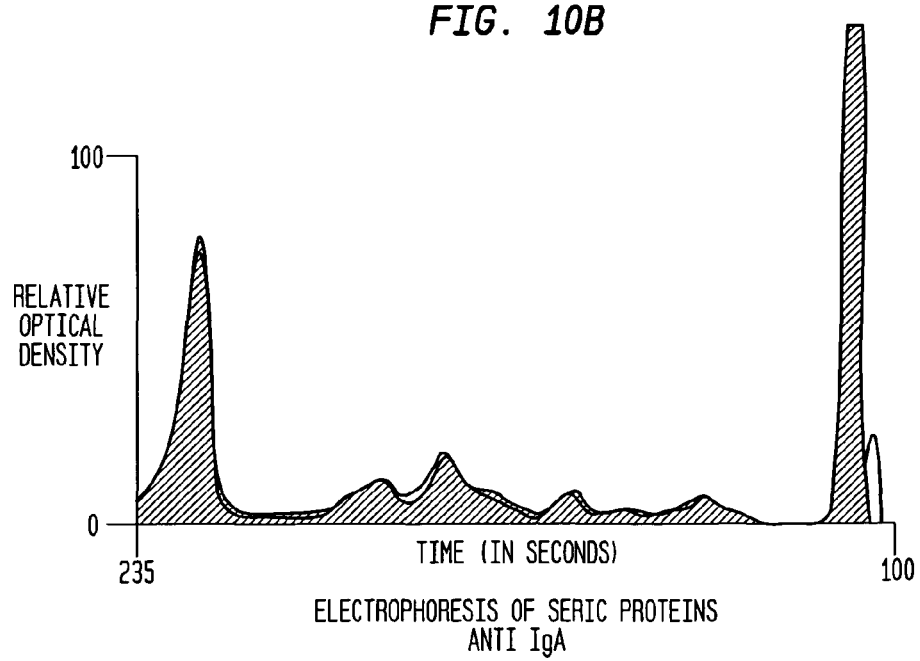

ELECTROPHORESIS OF SERIC PROTEINS
SERUM WITH PEAK SHOULDERING BETA-1 - ELP

ELECTROPHORESIS OF SERIC PROTEINS
SERUM WITH PEAK SHOULDERING BETA-1 - PENTAVALENT

ELECTROPHORESIS OF SERIC PROTEINS
SERUM WITH FREE LAMBDA AT GAMMA - ELP

ELECTROPHORESIS OF SERIC PROTEINS
SERUM WITH FREE LAMBDA AT GAMMA - TRIVALENT

ELECTROPHORESIS OF SERIC PROTEINS
SERUM WITH FREE LAMBDA AT GAMMA-ANTI LAMBDA

ELECTROPHORESIS OF SERIC PROTEINS
SERUM WITH FREE LAMBDA AT GAMMA-ANTI LAMBDA

ELECTROPHORESIS OF SERIC PROTEINS
SERUM WITH FREE LAMBDA AT GAMMA - ANTI-FREE KAPPA

ELECTROPHORESIS OF SERIC PROTEINS
SERUM WITH FREE LAMBDA AT GAMMA - ANTI-FREE LAMBDA

ELECTROPHORESIS OF SERIC PROTEINS
SERUM WITH M KAPPA AT GAMMA, PROTEIN BUFFER - ELP

ELECTROPHORESIS OF SERIC PROTEINS
ANTI IgG

ELECTROPHORESIS OF SERIC PROTEINS
ANTI IgA

ELECTROPHORESIS OF SERIC PROTEINS
ANTI IgM

ELECTROPHORESIS OF SERIC PROTEINS
ANTI KAPPA

ELECTROPHORESIS OF SERIC PROTEINS
ANTI LAMBDA

ANALYZING AND TYPING MONOCLONAL PROTEINS BY CAPILLARY ELECTROPHORESIS AND IMMUNODISPLACEMENT

FIELD OF THE INVENTION

The invention relates to the field of analyzing biological samples by capillary electrophoresis and immunodisplacement.

The invention relates especially to a method for analyzing biological samples by capillary electrophoresis in which electrophoretic separation of the constituents of the sample is accompanied by a treatment of the sample by an immunological technique. Within the context of the present invention, the term "immunosubtraction" designates suppression of a peak for certain proteins in the electrophoretic profile, as a result of immunodisplacement of that protein peak means displacement to another position in the profile.

In particular, the invention relates to a method that can be applied in diagnostic protocols, and especially concerns the investigation and typing in biological samples of proteins that bear witness to monoclonal disorders, also known as monoclonal gammapathies or paraproteinemias.

BACKGROUND OF THE PRESENT INVENTION

The normal development of B lymphocytes results in the production, on the surface of mature B lymphocytes, of immunoglobulins with isotypes M and G, initially having common isotypes. Plasmocytic disorders which are at the origin of monoclonal diseases result from a control default in the process of cell maturation into antibody secreting cells after exposure to a specific antigen of the surface immunoglobulin. In that situation, immunoglobulins having an affinity for an antigen to which the host has been exposed continue to be secreted after the disappearance of the antigen. In general, immunoglobulins of a given species are distributed into different classes of antibodies, each class being identified by an isotype, the different isotypes identified within a species being common to all normal individuals of that species. Immunoglobulins are generally formed from heavy chains (2 heavy chains) and light chains (2 light chains). Five heavy chain isotypes (M, G, A, D, E) and two light chain isotypes (kappa and lambda) have been identified in that four-chain structure. In addition to their isotype, immunoglobulins are characterized by determinants corresponding to differences between the individuals of a given species, termed allotypes, as well as by their idiotype, corresponding to a portion of the immunoglobulin molecule binding the antigen. Thus, the idiotype is characteristic of molecules produced by a given clone of antibody producing cells.

Plasmocytic diseases are thus particularly characterized by an alteration in the production of certain immunoglobulins or certain immunoglobulin chains, and detection and characterization of that alteration is of great clinical importance.

Electrophoretic analysis of a biological sample allows identification of seric proteins and determination of the quantity of those proteins, in particular of immunoglobulins. In an electric field, proteins migrate as a function of their size and charge, forming an electrophoresis profile comprising a series of peaks (also termed fractions), each corresponding to one or more proteins. The gamma fraction is especially formed by immunoglobulins, principally type G. In patients suffering from plasmocytic diseases leading to the secretion of monoclonal proteins (also termed Mc proteins), the quantity of immunoglobulins corresponding to one of the known isotypes may be significantly increased over the normal quantity, leading to a modification in the electrophoretic profile by modification of one or more peaks for the proteins separated from a serum sample.

The detection of monoclonal proteins, in particular the detection of an increase in the production of a particular immunoglobulin isotype, is thus of great importance when investigating plasmocytic diseases, but also when monitoring patients with paraproteinemias. As an example, it has been observed that, depending on the case and in particular during tumor development, the quantity of a seric Mc protein can be directly related to the progress of the disease. A Mc protein may thus constitute a tumoral marker which, when correlated with other symptoms, can be taken into account when making a diagnosis.

Plasmocytic diseases are not only concerned with the abnormal production of Mc proteins; pathological disorders associated with the production of Mc proteins that can be cited include lymphoid neoplasms, such as chronic lymphoid leukemia or lymphomas of B or T lymphocytic origin, certain non lymphoid proliferations such as chronic myeloid leukemia, and cancers of the breast or colon.

Monoclonal Mc proteins can also be produced in certain non malignant diseases such as cyrrhosis, sarcoidosis, parasitoses or Gaucher's disease. The production of monoclonal proteins is also detected in autoimmune diseases such as rheumatoid polyarthritis, myasthenia, or cold agglutinin disease.

By enabling detection of the presence of monoclonal proteins in biological samples and following the change in the detected monoclonal proteins with time, agarose gel and capillary electrophoresis, thus constitute the methods of choice with a view to establishing a diagnosis or monitoring patients.

Depending on the diseases concerned, the Mc protein is of a different nature, constituted either by an intact antibody molecule, or by a fragment of antibody. Thus, heavy chains or light chains can be produced alone. This is the case, for example, with Bence Jones proteins secreted in the urine of patients with myelomas, which are in the form of light chains alone.

The isotypes that are determined for the immunoglobulins allow the Mc proteins to be typed as a function of the nature of their heavy chain and/or as a function of the nature of their light chain. The technique used to type immunoglobulins thus allows the type of heavy and/or light chains associated with each monoclonal protein in a biological sample to be determined.

In addition to detecting the presence of said Mc proteins, it thus appears important to type them to enable the disease associated with them to be characterized. To this end, different approaches have already been proposed, such as column chromatography, agarose gel electrophoresis or capillary electrophoresis. In methods employing agarose gel electrophoresis, proteins from the biological sample are separated by electrophoresis in the form of an electrophoresis profile in which the proteins and in particular the globulins are revealed in the form of peaks or bands that may include a monoclonal protein, the nature of which must then be confirmed, for example by immunofixation on agarose gel. That technique combines two steps by using agarose gel electrophoresis then immmunoprecipitation. Several aliquots of the same biological sample are deposited in parallel on agarose gel, then an electric field is applied to separate the proteins, in particular the immunoglobulins. Each track is then incubated with a type of antibody that is specific to the types of immunoglobulins being investigated (IgG, IgA, IgM, kappa and lambda, and possibly free kappa, free lambda, IgD and IgE), leading to the formation of immunocomplexes between the immunoglobulins in the sample and the antibodies. After washing the gel to eliminate non-precipitated proteins, a staining step reveals the position of the immunocomplexes: in the absence of monoclonal proteins, only a diffuse stained background appears (corresponding to a multitude of monoclonal antibodies constituting the "polyclonal background"); in the presence of monoclonal proteins, stained bands are revealed in specific regions of the gel. Using a reference track (no antiserum), each monoclonal band that is visible on the gel can then be typed.

One typing technique used in capillary electrophoresis is immunosubtraction, as described in U.S. Pat. No. 5,228,960. That technique consists of incubating aliquots of a biological sample with specific antibodies that can subtract a given constituent (for example immunoglobulins) from said sample. That constituent remains adsorbed on the solid phase on which the antibody is fixed: thus, it is no longer present in the sample analyzed by capillary electrophoresis. The different treated aliquots from which certain immunoglobulins have been subtracted depending on the specificity of the antibodies used are then injected into the capillary, then the proteins contained in the aliquots are separated by applying an electric field to the terminals of the capillary. The profiles obtained are compared with an untreated aliquot profile.

Other techniques for identifying monoclonal proteins separated by capillary electrophoresis from a sample have been proposed, for example in European patent EP-B1-0 690 988. That European patent describes the combination of capillary electrophoretic separation with an immunosubtraction step with the aim of facilitating the classification of Mc proteins. In that patent, immunosubtraction is carried out "on-capillary" using a method which comprises a step for electrophoretic separation of a first portion of the sample into its different constituents, and detection of those constituents, then mixing a second portion of the sample with at least one partner that is capable of specifically binding a predetermined analyte contained in the sample, it being understood that the specific partner for binding has an electrophoretic mobility that differs from that of said analyte. The second portion of the sample is then separated into its different constituents by capillary electrophoresis and the constituents are detected. A step for comparing the separated constituents is then carried out with the constituents separated without the presence of specific partners binding a desired analyte.

EP-B1-0 690 988 states that the partner intended to bind the analytes is a modified molecule, in particular an anti-Mc protein antibody, which has undergone chemical modification so that its migration time in capillary electrophoresis takes it outside the gamma region of the electrophoretic profile. One chemical modification that is proposed for the antibodies is that which consists of reacting them with succinic anhydride to provide them with additional carboxylic functions, negative at alkaline pH. Under the analytical conditions described (pH 10), the overall negative charge of the antibodies is thus increased.

The conditions described for modifying the antibodies in EP-A-0 690 988 and the experimental results that are reported, which solely concern the analysis and separation of purified G immunoglobulins and not serum analysis, throw doubt on the pertinence of the proposed method when investigating monoclonal proteins in a "real" biological sample, for example in a serum.

SUMMARY OF THE INVENTION

The present invention thus proposes an alternative method that can be applied effectively to a biological sample, associating carrying out capillary electrophoresis to separate the constituents of a biological sample and immunosubtraction to allow typing of Mc proteins which may be present in the analyzed biological sample.

One advantage of the method of the invention is that it allows displacement outside the zone corresponding to the migration profile for the proteins of the sample, in particular outside the globulin migration zone, of the electrophoresis peak corresponding to a Mc protein when it is present in a biological sample and which has been separated by capillary electrophoresis. This displacement subtracts the peak representing the separated Mc protein from its expected position at the end of the migration step without interfering with the separation of other proteins in the sample. In contrast to the method described in U.S. Pat. No. 5,228,960, the monoclonal protein recognized by the antibody is present in the sample injected to carry out capillary electrophoresis. It is simply subtracted from the profile as it is displaced from its initial position. As a result, this method allows reliable reading of the results of the analysis, dissipating any possible confusion between neighboring peaks corresponding to separated proteins in the sample.

The invention also concerns antibodies which are chemically modified to provide them with additional chemical functions which are negative at alkaline pH (such as carboxylic functions) by reacting certain chemical functions of the antibody with a modifying agent: each of the modified chemical functions then provides the antibody with one or more additional negative charges. Those antibodies are then used for specific immunosubtraction/immunodisplacement of peaks corresponding to Mc proteins in a biological sample.

Compared with the starting antibodies which are already negatively charged when at an alkaline pH, the antibodies then prepared in the context of the invention have additional negative charges when at an alkaline pH because of the acquisition of functions such as additional carboxylic acid functions. These antibodies will henceforth be termed "negatively surcharged modified antibodies" or "modified antibodies".

The invention also concerns kits for separating proteins from a biological sample by capillary electrophoresis and detection by immunosubtraction to identify them and, if appropriate, to quantify them, from monoclonal proteins that may be contained in a test biological sample.

The invention also concerns a method for preparing chemically modified antibodies to graft onto them additional charges which are negative at an alkaline pH (negatively surcharged modified antibodies), under conditions that allow their use in immunosubtraction. Thus, the invention concerns a method for capillary electrophoretic analysis of a biological sample, comprising employing negatively surcharged modified antibodies so that they migrate in a zone located outside the migration zone for proteins of the biological sample when they are separated during electrophoresis, said antibodies having antigenic specificity for a predetermined monoclonal protein.

BRIEF DESCRIPTION OF THE DRAWINGS

FIGS. 1 to 13 show examples of detection of monoclonal proteins in different biological samples and typing of said monoclonal proteins, and thus improve prognosis and treatment of these diseases. In FIGS. 2 to 13, the gray surface of the profile represents the seric proteins separated in the presence of the antibodies of the invention; the profile of the seric proteins separated outside the presence of the antibodies also appears, but with a fainter line. The profile of separated proteins not treated with the antibodies of the invention also appears alone in each figure, under the designation ELP.

FIG. 2 is an electrophoretic profile of serum containing monoclonal type A lambda protein migrating to beta-2 on Capillarys with no antibodies designated ELP.

FIG. 2b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 2c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 3 is an electrophoretic profile of serum containing monoclonal type G lambda protein migrating to beta-1 on Capillarys with no antibodies designated ELP.

FIG. 3b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 3c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 4 is an electrophoretic profile of serum containing monoclonal type A kappa protein migrating between beta-1 and alpha-1 on Capillarys with no antibodies designated ELP.

FIG. 5 is an electrophoretic profile of serum containing a monoclonal type G lambda protein migrating to gamma on Capillarys with no antibodies designated ELP.

FIG. 6 is an electrophoretic profile of serum containing monoclonal type A lambda protein migrating between beta-1 and beta-2 on Capillarys with no antibodies designated ELP.

FIG. 7 is an electrophoretic profile of serum containing monoclonal type M kappa protein migrating to gamma on Capillarys with no antibodies designated ELP.

FIG. 8 is an electrophoretic profile of serum containing monoclonal free lambda type protein migrating to gamma on Capillarys with no antibodies designated ELP.

FIG. 8f is an electrophoretic profile of serum containing anti-free kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 8g is an electrophoretic profile of serum containing anti-free lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 9 is an electrophoretic profile of serum containing a monoclonal type G kappa protein migrating to gamma on Capillarys with an anti-human IgG antibody with no antibodies designated ELP.

FIG. 10 is an electrophoretic profile of serum containing a monoclonal type G kappa protein migrating to gamma on Capillarys with no antibodies designated ELP.

FIG. 10a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 10b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

FIG. 11 is an electrophoretic profile of serum shouldering a peak at beta-1 on Capillarys with no antibodies designated ELP.

FIG. 12 is an electrophoretic profile of serum containing a free lambda type Mc protein migrating to gamma on Capillarys with no antibodies designated ELP.

FIG. 13 is an electrophoretic profile of serum containing a type M kappa Mc protein migrating to gamma on Capillarys with no antibodies designated ELP.

DETAILED DESCRIPTION

Figure 1A:
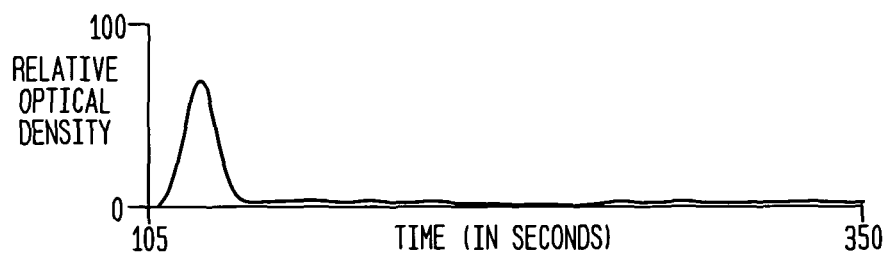
FIG. 1a is an electrophoretic profile of seric proteins containing anti-human IgG, DAKO, before modification with 1,2,4-benzenetricarboxylic acid anhydride. Its migration time is 122 seconds.

When separating the proteins of a biological sample in a capillary filled with an electrolyte, proteins migrate under the effect of an electric field: the proteins are then entrained in a migration from the anode towards the cathode. The difference between their own electrophoretic flow (linked to the charge on the protein) and the electroosmotic flux (linked to the charge on the internal surface of the capillary) allows the proteins to be detected to be separated.

The proteins of a sample injected into the capillary thus define an electrophoretic migration profile which can be cut into a plurality of zones, as illustrated in the figures of the present application, corresponding to gamma (closest to the cathode), beta-2, beta-1, alpha-2, alpha-1 and albumin zones (the latter zone being closest to the anode). Immunoglobulins contained in a biological sample, including Mc proteins, migrate from zone alpha-1 to zone gamma.

With the aim of allowing electrophoretic separation of monoclonal proteins contained in a biological sample and their reliable typing using an immunosubtraction reaction, the inventors have devised conditions for carrying out immunosubtraction which allow the peak corresponding to a monoclonal protein to be subtracted from the migration profile for proteins of the sample (and in particular the migration profile for globulins) and its displacement outside the region between the gamma zone and the alpha-1 zone.

More precisely, the monoclonal protein investigated in the sample is not subtracted from the analyzed medium but displaced under the effect of it binding with a negatively surcharged modified antibody that specifically recognizes it, under conditions such that the complex formed between said monoclonal protein and said modified antibody is displaced outside the migration profile for globulins in the sample (the globulins correspond to the gamma, beta-2, beta-1, alpha-2 and alpha-1 electrophoretic fractions on the electrophoretic profile).

More precisely still, the (Mc protein-antibody negatively charged at alkaline pH) complex is in the most anodic zone of the separated protein profile after electrophoretic migration.

The modified antibody-Mc protein complex is thus visible outside the profile defined by the separated immunoglobulins, and in particular is spaced from the gamma zone towards the albumin, possibly being visible close to albumin and alpha-1, without this interfering with any detection of an anodic monoclonal protein (i.e. migrating to alpha-1/alpha-2) since the mobility of the complex is intermediate between that of the monoclonal protein and that of the modified antibody.

The modified antibody is in principle supplied in excess for the reaction and the fraction of unreacted antibody is visible towards the anode beyond the peak corresponding to albumin (i.e. migrates more anodically than albumin).

A first method in accordance with the invention for capillary electrophoretic analysis of a biological sample and immunosubtraction comprises the following steps:
  a) separating the constituents of a first aliquot portion of the biological sample by capillary electrophoresis, in the presence of negatively surcharged modified antibodies having a determined antigenic specificity and which can form a complex of the antigen-antibody type with a monoclonal protein that may be present in the biological sample, and detecting the separated constituents of the biological sample;
  b) comparing the electrophoretic profile obtained in step a) with an electrophoretic profile of the constituents of another aliquot profile from the same sample separated by capillary electrophoresis in the absence of said negatively surcharged modified antibodies with a determined antigenic specificity.

It will be observed that biological samples normally comprise a polyclonal fraction of immunoglobulins constituting a "polyclonal background" located in the gamma region (or close thereto) of the electrophoretic profile. Said polyclonal immunoglobulins appear in the form of a peak that is wider than that of Mc immunoglobulins (as they contain a large number of immunoglobulins with very similar mobilities), under conditions for carrying out capillary electrophoresis that is suitable for separating Mc proteins; this polyclonal background can be reduced when bringing the sample into contact with negatively surcharged modified antibodies, depending on the type of constituent immunoglobulins (G, A, M, kappa or lambda). The distinction between the monoclonal peak and polyclonal background is made in this case by marking the focused Mc peak to be detected with respect to the wide polyclonal peak.

In a preferred implementation of the invention, aliquot portions of a given biological sample are brought into contact in parallel with different antibodies forming a series of negatively surcharged modified antibodies, each type of antibody in this series having a predetermined antigenic specificity for an immunoglobulin isotype.

Thus, in parallel, it is possible to carry out an analysis of the same biological sample with said modified antibodies with different specificity, the antigenic specificity of said antibodies being selected as a function of the investigated monoclonal proteins which would be recognized by said antibodies and as a function of the number of capillaries in parallel on the electrophoresis apparatus.

In accordance with another particular implementation of the invention, in one of the methods described above, the biological sample is divided into at least two aliquot portions and the method comprises the following steps, prior to separating the constituents of the biological sample by electrophoresis:

1) bringing a medium containing the negatively surcharged modified antibodies having a determined antigenic specificity into contact with one aliquot portion of the biological sample under incubation conditions that allow the immunological reaction between said antibodies and a target protein specifically recognized by said antibodies when it is present in the biological sample, and bringing another aliquot portion of the biological sample into contact with said medium which is, however, free of modified antibodies;
2) injecting the aliquot portions of the biological sample incubated in step 1) into the electrophoresis capillary.

In a further particular implementation of the invention, the capillary electrophoretic analysis method comprises the following steps, prior to separating the constituents of the biological sample by electrophoresis:

1) injecting a medium containing negatively surcharged modified antibodies having a determined antigenic specificity into the electrophoresis capillary, and injecting said medium which is, however, free of said modified antibodies into another electrophoresis capillary;
2) injecting the biological sample into the electrophoresis capillary treated in accordance with step 1), under conditions that allow the immunological reaction between the antibodies and the target protein or proteins when it (they) is (are) present in the biological sample.

To analyze a biological sample, when the negatively surcharged modified antibodies comprise n types of antibodies with different predetermined specificities, the biological sample is separated into at least n+1 aliquot portions.

The antibodies used to prepare the negatively surcharged modified antibodies are immunoglobulins selected from anti-IgG, anti-IgA, anti-IgM, anti-IgE, anti-IgD, anti-kappa, anti-lambda, free anti-kappa and free anti-lambda.

Preferably, the antibodies are selected from anti-IgG, anti-IgA, anti-IgM, anti-kappa and anti-lambda antibodies. In a particular implementation of the invention, a series of antibodies comprising these 5 antibodies is used. In a further implementation of the invention, a mixture of all or a portion of these antibodies is used, for example a mixture of 5 antibodies (pentavalent antiserum) or a mixture of 3 antibodies (trivalent antiserum), for example containing anti-IgG, IgA, IgM heavy chain antibodies.

Implementation of the method of the invention can also be limited to the use of only some of the antibodies identified above.

To obtain negatively surcharged modified antibodies which can be used in the context of the invention, antibodies having the selected antigenic specificity are reacted with a compound that supplies the additional negative charges at alkaline pH, for example a negatively charged anhydride. As an example, it is possible to react amine functions of the antibodies with an anhydride, resulting in the formation of an additional carboxylic acid function on the antibody (and thus an additional negative charge at an alkaline pH) for each modified amine function.

To produce said negatively surcharged modified antibodies, the anhydride employed is advantageously a benzene tricarboxylic anhydride. This anhydride supplies two carboxylic acid functions (and thus two additional negative charges at an alkaline pH) for each modified amine function: a first function due to the reaction of the anhydride with the amine function; a second function due to its structure. The anhydride of the invention will then be termed a negatively charged anhydride as it carries at least one carboxylic acid function which is negatively charged at an alkaline pH.

A sufficiently modified antibody, i.e. sufficiently negatively charged at an alkaline pH, can be obtained by reacting the antibody with the negatively charged anhydride by extemporaneously dissolving the anhydride, in particular benzene tricarboxylic anhydride, in dimethylformamide (DMF) and bringing the dissolved anhydride into contact with the antibody in solution to supply the antibody with negative charges, said reaction being carried out at 37° C. under conditions that allow the carboxylic acid functions to graft to the antibody.

Grafting the anhydride to the antibody is carried out with greater efficacy if the solution of the anhydride in DMF is brought into contact with the antibody at the last possible moment to obtain antibodies with additional carboxylic acid functions (and thus additional negative charges at an alkaline pH) and to prevent alteration of the anhydride by the water contained in the antibody solution.

One method for preparing modified antibodies will be described below in more detail.

To supply additional carboxylic acid functions (and thus additional negative charges at an alkaline pH) to the antibody, in a variation, it is possible to use a carboxylic acid (supplying negative charges at an alkaline pH) associated with a coupling agent, for example EDCI (1-(3-dimethylaminopropyl)-3-ethylcarbodiimide hydrochloride). As an example, it is possible to use mellitic acid which reacts with the amine functions of the antibodies in the presence of EDCI.

The modified antibodies employed in the capillary electrophoretic analysis method of the invention are normally in excess with respect to the target protein which they recognize when it is present in the biological sample.

This excess can not only allows the complete disappearance of the target Mc protein of the protein profile, but also allows an optimum positioning of the modified antibody-Mc protein complex on the profile: too low a ratio between the modified antibodies with a predetermined antigenic specificity and the target proteins of the sample recognized by that antibody would not allow total subtraction of the Mc peak and would produce a more cathodic migration of the complex than if the ratio were higher.

In a particular implementation of the invention, the concentration of negatively charged antibodies of each specificity employed for immunosubtraction is about 10 g/l.

The invention also concerns negatively surcharged modified antibodies which are the product of the reaction of antibody with an anhydride carrying at least two carboxylic acid functions, preferably 1,2,4-benzene tricarboxylic anhydride.

The antibodies used in the capillary electrophoresis and immunosubtraction analysis method are thus advantageously the product of reacting antibody with a negatively charged anhydride, said reaction comprising extemporaneously dissolving the anhydride in dimethylformamide ((DMF) and bringing the dissolved anhydride into contact with the antibody in solution to allow the anhydride and antibody to react, said reaction being carried out at 37° C. under conditions that allow grafting of additional chemical functions to the antibody, in particular carboxylic acid functions, which are at an alkaline pH.

The method for analyzing biological samples can be employed in different types of biological samples such as serum, plasma, urine or cephalorhachidian fluid samples.

Depending on the nature of the biological sample used and/or its origin (i.e. depending on the medical history of the patient), interpretation of the results from electrophoretic separation take into account interference which may occur between the negatively surcharged modified antibodies and the proteins of the sample. Such interference can be observed and analyzed by the skilled person and has been observed in samples containing fibrinogen, namely plasma or serum samples from certain patients treated with anticoagulating compounds. The inventors have observed that fibrinogen can react in a non specific reaction (i.e. a reaction which is not of the antigen-antibody type) with the negatively surcharged modified antibodies of the invention. In this case, when fibrinogen is present, which is shown in an electrophoretic profile by the presence of a peak between zones β and γ, that peak is removed from its normal migration zone after treating the sample with the negatively surcharged modified antibodies of the invention, this removal occurring regardless of the specificity of the negatively surcharged modified antibodies employed. In other words, the peak marking the presence of fibrinogen in the sample is revealed only in the control electrophoretic profile (ELP) and disappears in the profile of proteins which undergo immunological reactions with the negatively surcharged modified antibodies (by immunodisplacement to a zone outside this profile).

The conditions for carrying out capillary electrophoresis in a liquid mode are the conditions which are normally employed by the skilled person for the steps of injecting the sample into the capillary tube and separating the constituents from the sample by electrophoretic migration under the influence of an electroendosmosis current. Those steps comprise the use of electrophoresis buffers such as those described in International patent applications WO-A-02/057736 and WO-A-02/057737, it being understood that the electrophoresis buffers are selected to allow separation of Mc proteins in the form of peaks. Conditions for carrying out capillary electrophoresis are, for example, conditions under which the CAPILLARYS® (SEBIA) automated machine can be used, including buffers sold by SEBIA under the trade name CAPILLARYS® B1B2+, CAPILLARYS®protein(e) 6 and CAPILLARYS®Protein(e) 5.

As an example, the analysis buffer used for electrophoretic migration is advantageously an alkaline buffer the pH of which is in the range 9 to 11, preferably about 10, comprising in particular a buffer compound and at least one additive that can enhance the ionic strength of the analysis buffer.

Under the influence of the chemical modification to the mobility of antibodies used to carry out the immunosubtraction step, the capillary electrophoretic analysis method described above can remedy the consequences which may result from co-migration of monoclonal proteins with the protein constituents of the sample during the electrophoretic separation step. The method of the invention can avoid interference between the monoclonal proteins recognized by the negatively surcharged modified antibodies and the other proteins constituting the biological sample. This essential advantage for reliable detection of monoclonal proteins in a biological sample results from the fact that the Mc protein-modified antibody complex migrates after the globulins and thus allows typing of the Mc protein recognized by the negatively surcharged modified antibody regardless of the position of the monoclonal protein during electrophoretic migration.

Further, immunosubtraction of the peak corresponding to the Mc protein-negatively charged antibody complex is total in the sense that the peak which would correspond to the monoclonal protein is not longer detectable in the zone corresponding to the migration profile for globulins from the biological sample.

As a consequence, the method of the invention is advantageously applicable to detecting and typing all types of monoclonal IgG, IgA, IgM, IgD, IgE and free chain immunoglobulins regardless of their mobility, since the gamma, beta and alpha zones of the migration profile are without interference with the migration zone for the negatively surcharged modified antibody and the complex which it forms with the Mc proteins when present in a biological sample.

The method of the invention is thus applicable to capillary electrophoretic analysis of monoclonal proteins in a biological sample.

To detect and type monoclonal proteins in a biological sample, a plurality of capillary analyses are advantageously carried out in parallel, the biological sample being divided into different aliquot portions, the number of aliquot portions being at least equal to the number of types of immunoglobulins used to investigate the Mc proteins.

To carry out typing of Mc proteins in a biological sample, at least 6 parallel capillary analyses are normally carried out.

Advantageously, the negatively surcharged modified antibodies are immunoglobulins the antigenic specificity of which is selected from anti-IgG, anti-IgA, anti-IgM, anti-kappa and anti-lambda and/or anti-free kappa and/or anti-free lambda immunoglobulins.

Anti-IgD and/or anti-IgE immunoglobulins can also be added.

In addition to the fact that the Mc protein which may be present in the biological sample can be typed by the method of the invention, said Mc protein, when present, can be quantified. To this end, the surface area of the peak corresponding to the Mc protein that has been subtracted from the profile is determined.

The method of the invention can also be used to identify other proteins (not immunoglobulins) which are visible on the electrophoretic profile; as an example, modified antibodies with anti-human-haptoglobin, -alpha 1 antitrypisn, -C3 complement, -C4 complement, -transferrin specificity, -RBP, β2-microglobulin, -α1-microglobulin, or antibodies with other specificities can be used. With these antibodies, it would be possible to identify proteins constituting a fraction of an electrophoretic profile, or to pick out a particular phenotype of these proteins having a mobility other than normal.

The conditions for implementing the invention described in the present application for detecting proteins other than immunoglobulins can be applied analogously.

The invention also concerns a method for preparing negatively surcharged modified antibodies, comprising the steps of:
  extemporaneously dissolving an anhydride comprising at least one carboxylic acid function in dimethylformamide (DMF);
  bringing the antibodies into contact with the dissolved anhydride under conditions that allow the anhydride and antibody to react to obtain a modified antibody negatively surcharged at an alkaline pH.

The anhydride selected to provide the antibody with additional negative charges at an alkaline pH is an anhydride having at least one carboxylic acid function.

The anhydride selected to supply the additional negative charges at an alkaline pH is preferably benzene tricarboxylic anhydride.

The preparation of the negatively surcharged modified antibodies will be described in detail in the experimental section.

It should be emphasized that to be effective when supplying negative charges, the above steps advantageously comprise dissolving the anhydride in pure dimethylformamide then mixing said anhydride solution at the moment it is grafted with the antibody, i.e. subsequently.

Observing these conditions prevents destruction of the anhydride by the water contained in the antibody solution, as that destruction would alter the efficacy of the preparation of the charged antibodies, diminishing the addition of negative charges at an alkaline pH.

Preferably, the reaction between the anhydride and the antibody, in particular between benzene tricarboxylic anhydride and the antibody, is carried out at a temperature of 37° C. or at an appropriate temperature to increase the number of anhydride molecules grafted onto the antibody, and for example for a period of about one hour.

Before contact with the anhydride, the antiserum to be grafted is advantageously dialyzed against a solution of PBS buffer or phosphate buffer. Further, when the antibody is brought into contact with the anhydride solution in DMF, sodium hydroxide is preferably added, which can better buffer the carboxylic acid functions of the benzene tricarboxylic anhydride already present and those which form during the reaction of the anhydride with the antibody (to keep the pH in the reaction medium neutral, to allow reaction of the anhydride with the amine functions of the antibody to continue).

In a particularly preferred implementation of the invention, during contact with the anhydride in DMF, the antibody, previously dialyzed against a PBS buffer or a phosphate buffer at a pH of 7.4, is brought into contact with 5N sodium hydroxide, and preferably the number of equivalents of sodium hydroxide added equals the number of carboxylic acid functions (1) formed during the reaction and (2) supplied by the anhydride. The modified antibodies are then dialyzed in a medium which preserves the antibodies, then said solutions are brought to a suitable working concentration (about 10 g/l) to place it under conditions in which the antibody/antigen ratio is optimal.

The invention also concerns negatively surcharged modified antibodies characterized in that they comprise carboxylic acid functions grafted to endow them with a capacity for electrophoretic migration outside the migration profile for immunoglobulins of a biological sample separated under the same separation conditions by capillary electrophoresis. Said negatively surcharged modified antibodies preferably result from carrying out one of the methods described above.

The negatively charged antibodies can be monoclonal antibodies. Alternatively, they may be polyclonal antibodies.

Contact between the antibody and the antigenic proteins of the sample can be made in two ways: mixing the modified antibody solution with the biological sample, preferably diluted, in the sample support, for example in the Capillarys head, prior to injection into the capillary, or alternatively successive injections of the modified antibody solution then the diluted sample into the capillary. This second mode for carrying out the contact step allows an antigen/antibody reaction to take place inside the capillary (in-capillary), which is as effective as the conventional mode of mixing the 2 solutions in the head or other sample support and is rendered possible by the differences in mobility of the modified antibodies with respect to the proteins of the sample and the order of injecting the two solutions: the modified antibodies have a much lower mobility than the proteins of the sample (because of their large negative charge) and being injected first, and injecting the sample after that of the modified antibodies causes passage of the sample through the antibody zone and thus allows subtraction from the protein profile of antigens recognized by the antibodies.

The invention also concerns a kit for detecting monoclonal proteins in a biological sample, comprising antibodies of the invention and other components, for example the medium intended to contain the antibodies, however without the antibodies (to obtain the reference profile) and/or electrophoresis buffers and/or solutions for rinsing the capillaries and/or specific reduced volume dilution heads and/or a diluent for the sample to be analyzed, which can, for example, allow good superimposition of the various curves obtained during the different analyses. This kit optionally comprises instructions for carrying out the electrophoretic and immunodisplacement analysis to reveal and type the Mc proteins.

Preferably, said kit contains a series of antibodies with anti-IgG, anti-IgA, anti-IgM, anti-kappa and anti-lambda specificities.

Another type of kit can contain a mixture of antibodies with anti-IgG, anti-IgA, anti-IgM, anti-kappa and anti-lambda specificities. This mixture, which can be termed a pentavalent antiserum, can confirm the monoclonal nature of a peak appearing in the electrophoretic profile or of a malformation in a fraction of that profile. Said kit is particularly interesting as Mc immunoglobulins can appear not only in the gamma zone, but also in beta and alpha zones, and may be masked by proteins that normally appear in these zones on the capillary electrophoresis profile obtained. In this implementation of the invention, the sample is tested on two tracks: one reference track (containing only antibody medium, without the antibodies) and a track that can reveal the presence of a monoclonal peak on the electrophoretic protein (using pentavalent antiserum).

Another type of kit can contain a mixture of antibodies with anti-heavy chain specificity ($\gamma$, $\alpha$ and $\mu$, anti-IgG, anti-IgA, anti-IgM which can be termed trivalent antiserum) and/or antibodies with anti-light chain, kappa and lambda (free and bound) specificity, and/or antibodies with anti-free light kappa and lambda chain specificity. This kit could detect and identify Bence Jones proteins or free light Mc (kappa or lambda) chains in human urine or serum by capillary electrophoresis. In this implementation, when these antiserums are employed, the sample is tested on 6 tracks: a reference track (containing only antibody medium, with out the antibodies), 5 tracks for characterizing the Mc band or bands: the presence of heavy chains using trivalent antiserum, and of the light chain type (kappa or lambda; free or bound).

The mixtures of modified antibodies can be obtained by modification of a mixture of untreated antibodies or by mixing antibody already modified by antibody type. In the context of the invention, producing a mixture of antibodies which have been modified in advance to be negatively surcharged is preferred.

In the context of the invention, the results of electrophoretic separation can be presented as shown in the examples, in the form of electrophoretic profiles wherein the peak corresponding to the protein identified by a specific immunological reaction with negatively surcharged antibodies has disappeared from the profile.

Alternatively, these results can be presented in the form of electrophoretic profiles which only show the peak corresponding to the protein identified by a specific immunological reaction with the negatively surcharged antibodies. In the context of carrying out the method of the invention, this peak disappears from the profile of separated proteins. However, the results are processed so that they only show that peak.

To this end, appropriate data processing techniques can be used to subtract each electrophoretic profile of an aliquot portion of the sample under consideration treated with a negatively surcharged modified antibody, from the profile of an untreated aliquot portion of the same sample. Subtracting all of the profiles of the processed aliquot portions results in an image of the type obtained with immunofixation.

Other characteristics and advantages of the invention will become apparent from the following examples and figures which illustrate the invention.

EXAMPLES

Capillary Electrophoresis

Capillary electrophoresis of clinical samples was carried out on a CE apparatus equipped with 8 fused silica capillaries with an internal diameter of 25 microns (CAPILLARYS®, Sebia). Detection was carried out at 200 nm. The samples were placed in the sample feeder of the apparatus and automatically injected by hydrodynamic injection. The samples were separated in less than 5 minutes by application of an electric field of about 400 V/cm. The capillary was rinsed before each analysis with 0.25M sodium hydroxide, then with the analysis buffer.

Protocol for Modifying Antibodies with Tricarboxylic Anhydride a) 10 ml of antiserum to be grafted (anti-human IgG, A, M, anti-kappa or lambda, DAKO, Denmark), 10 g/l, was dialyzed against a phosphate buffer solution, 100 mM, pH 7.4.

b) A solution of 1,2,4-benzenetricarboxylic anhydride, 100 mM, was prepared in DMF.

c) The dialyzed antibody solution was mixed with 5N sodium hydroxide then with the anhydride solution in DMF (213 µl 5N sodium hydroxide+10 ml of antibody solution+5.33 ml of anhydride in DMF).

d) The reaction medium was then placed, with gentle agitation, on a rocker for one hour at 37° C.

e) The mixture was then dialyzed against the 100 mM, pH 7.4 phosphate buffer solution, changing the dialysis liquid several times.

f) Once dialysis was complete, the column was placed in powdered PEG 6000 for 1 h.

g) Once concentration was complete, the latter was dialyzed against 100 mM, pH 7.4 phosphate+1 g/l of sodium nitride.

h) The volume of the column was brought to 10 ml with a solution of 100 mM, pH 7.4 phosphate+1 g/l of sodium nitride.

i) The solution obtained was filtered on a membrane with a porosity of 0.45 µm then stored at 4° C. Any other storage medium could be used provided that its ionic strength was sufficient to ensure the antibodies were preserved (i.e., close to that of physiological water).

Protocol for Modifying Antibodies with Mellitic Acid a) 10 ml of antiserum to be analyzed (anti-human IgG, A, M, anti-kappa or anti-lambda, DAKO, Denmark), 10 g/l, was dialyzed against a phosphate buffer solution, 40 mM, pH 7.4.

b) 50 µl/ml of 5N sodium hydroxide was added.

c) Add (18 mg/ml of mellitic acid then 50 mg/ml of EDCI).

d) The reaction medium was placed, with gentle agitation, on a rocker for one hour at 37° C.

e) The mixture was dialyzed against the 100 mM, pH 7.4 phosphate buffer solution, changing the dialysis liquid several times.

f) Once dialysis was complete, the column was placed in powdered PEG 6000 for 1 h.

g) Once concentration was complete, the latter was dialyzed against 100 mM, pH 7.4 phosphate+1 g/l of sodium nitride.

h) The volume of the column was brought to 10 ml with a solution of 100 mM, pH 7.4 phosphate+1 g/l of sodium nitride.

i) The solution obtained was filtered on a membrane with a porosity of 0.45 µm then was stored at 4° C.

Serum Immunotyping Protocol

The CAPILLARYS® (SEBIA) is an apparatus which carries out 8 capillary analyses in parallel. The immunotyping head is a CAPILLARYS® head specific for typing constituted by 6 100 µl wells and a 400 µl double well. It contains 60 µl of 100 mM phosphate in well 1, 60 µl of modified anti-IgG in well 2, of modified anti-IgA in well 3, of modified anti-IgM in well 4, of modified anti-kappa in well 5, of modified anti-lambda in well 6, and the double well 7/8 contains 380 µl of immunotyping diluent (0.02M benzyl alcohol in the analysis buffer used by Sebia).

a) The tube of serum to be typed is brought into position 1 on the CAPILLARYS carrier on which an "immunotyping" head has been placed.

b) The carrier is introduced into the apparatus: the automatic machine then dilutes the serum by 1/20 in the double well 7/8, the double well is homogenized and 40 µl is distributed into each of wells 1 to 6, homogenizing each of those wells.

c) Capillary analysis is then carried out under the following conditions:

The analysis buffer can be Sebia CAPILLARYS® B1B2+ or Sebia CAPILLARYS® Protein buffer;

B1B2+ buffer: temperature 32° C., migration tension 7 kV, acquisition window 100-235 s, injection 250 mbars*5 s;

Sebia CAPILLARYS® Protein(e) buffer: temperature 37° C., migration tension 6.5 kV, acquisition window 110-275 s, injection 250 mbars*5 s;

d) The capillary analysis obtained in well 1 is compared with that of the five subsequent wells to type the analyzed serum.

Operating Conditions for Particular Serums:

If the serum has a low gamma fraction, dilution in the diluent at b) is $1/10^{th}$. The gamma fraction is considered to be low if its analysis on the CAPILLARYS® apparatus with B1B2+ buffer gives a value less than the normal values defined for said fraction with this buffer, i.e. below approximately 10% (or <7.5 g/l).

If the serum has a gamma fraction of more than about 20 g/l, the dilution in the diluent at b) is $1/40^{th}$.

Variation in Protocol when Immunotyping a Serum: In-Capillary Immunosubtraction

In this case, 2 heads are used:

1 head constituted by 6 wells containing: 100 µl of 100 mM phosphate in well 1, 100 µl of modified anti-IgG in well 2, of modified anti-IgA in well 3, of modified anti-IgM in well 4, of modified anti-kappa in well 5, of modified anti-lamda in well 6;

1 head for serum dilution constituted by 7 wells containing: 380 µl of immunotyping diluent (0.02 M benzyl alcohol in Sebia CAPILLARYS® B1B2+ buffer) in double well 7/8;

a) A first carrier containing the antiserum head is introduced into the apparatus; the automated machine then injects said antibodies into the capillaries (250 mbars*5 s).

b) A second carrier containing the serum diluting head and a tube of serum in position 1 is then introduced into the apparatus: the automatic machine then makes a $1/20^{th}$ dilution in double well 7/8, the double well is homogenized and distributed into wells 1 to 6 (40 μl of 1/20$^{th}$ serum+60 μl of analysis buffer per well); the diluted sera are then injected into the capillaries (250 mbars*5 s).

c) The analysis buffer can be Sebia CAPILLARYS® B1B2+ buffer or Sebia CAPILLARYS® Protein(e) buffer:
B1B2+ buffer: temperature 32° C., migration tension 7 kV, acquisition window 100-235 s;
Sebia CAPILLARYS® Protein (e) buffer: temperature 37° C., migration tension 6.5 kV, acquisition window 110-275 s.

d) The capillary analysis obtained in well 1 is compared with that of the five subsequent wells to type the serum.

Results

Example 1

Figure 1B:
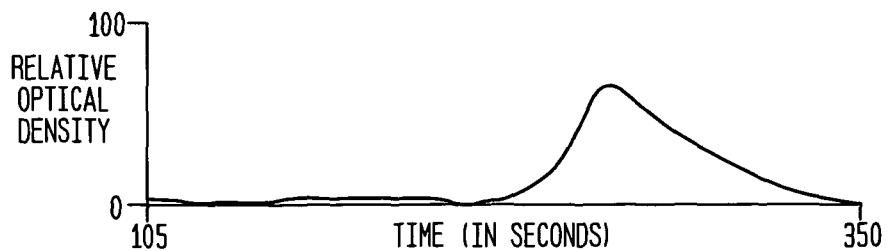
FIG. 1b is an electrophoretic profile of seric proteins containing anti-human IgG, DAKO, after modification with 1,2,4-benzenetricarboxylic acid anhydride Its migration time is 267 seconds.

Analysis of an anti-human IgG, DAKO, before and after modification with 1,2,4-benzenetricarboxylic anhydride on CAPILLARYS® with Sebia CAPILLARYS® B1B2+ buffer (acquisition window 105-350 s); modification of the antibody strongly retarded its migration: its migration time changed from 122 to 267 s (FIGS. 1a and 1b).

Example 2

Figure 2:
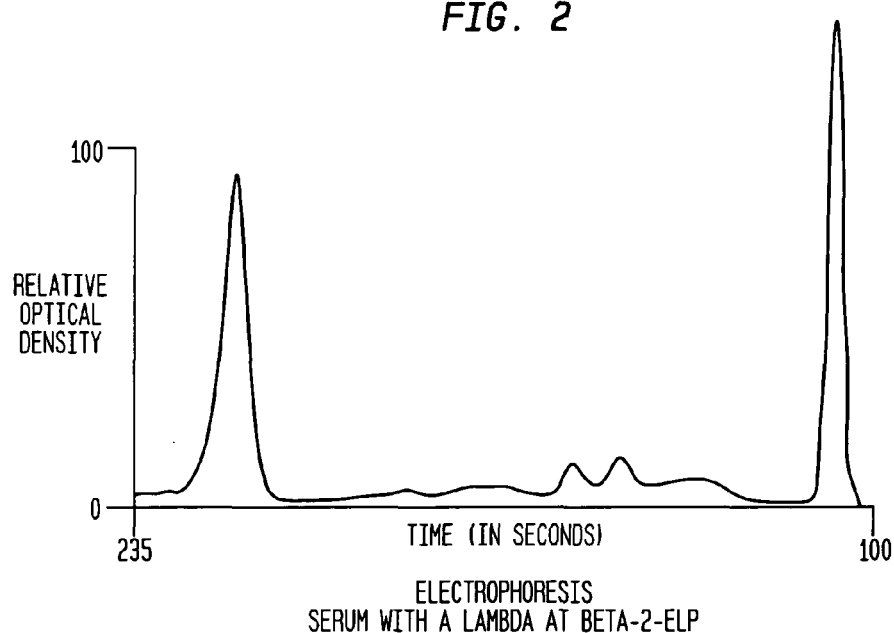
Figure 2A:
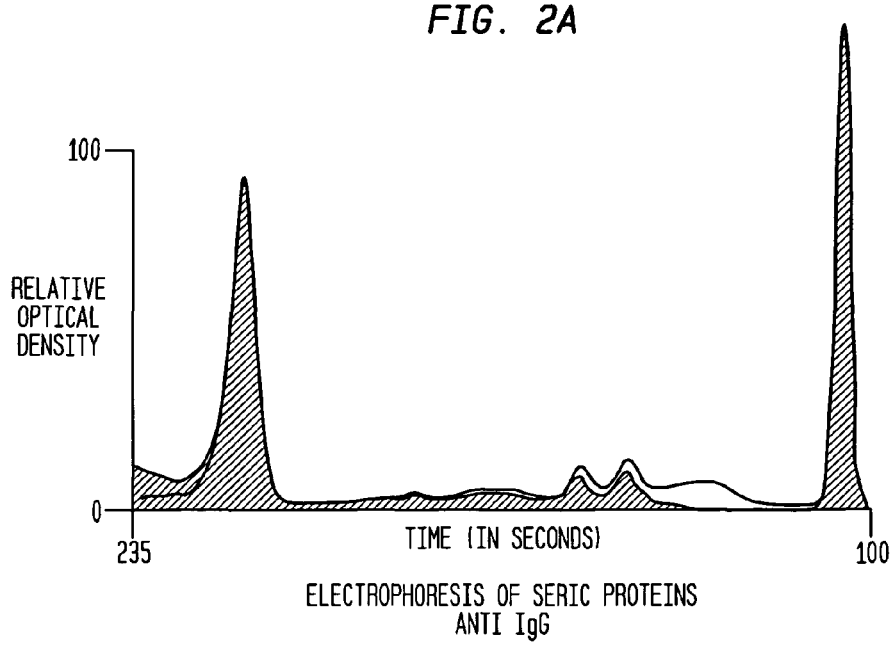
FIG. 2a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 2D:
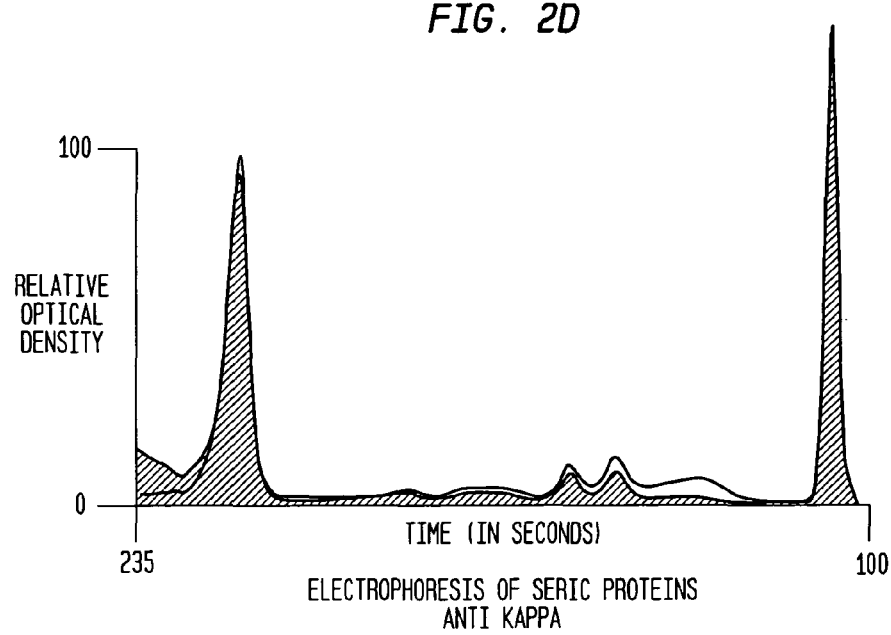
FIG. 2d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 2E:
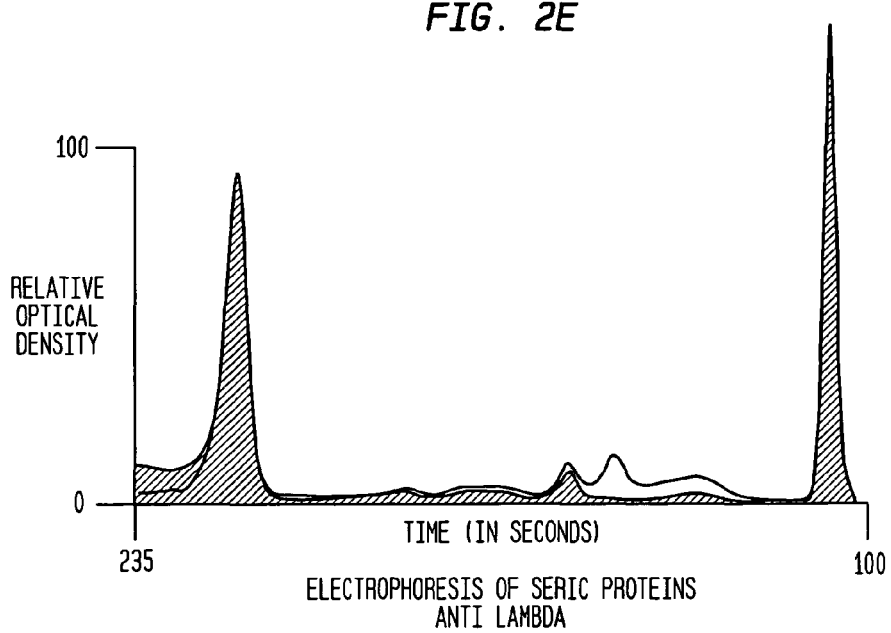
FIG. 2e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

Immunotyping of a serum containing a monoclonal type A lambda protein migrating to beta-2 on CAPILLARYS® with Sebia CAPILLARYS® B1B2+ buffer (acquisition window 100-235 s): 6 aliquots of this serum were mixed with 5 antibodies modified with 1,2,4-benzenetricarboxylic anhydride (anti-IgG, -IgA, -IgM, -kappa, -lambda) and with the medium for said antibodies (no antibodies: ELP track). Comparison with the ELP track (in black; FIG. 2) clearly showed the disappearance of the monoclonal peak at beta-2 for the aliquots treated with anti-IgA and anti-lambda. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 3

Figure 3:
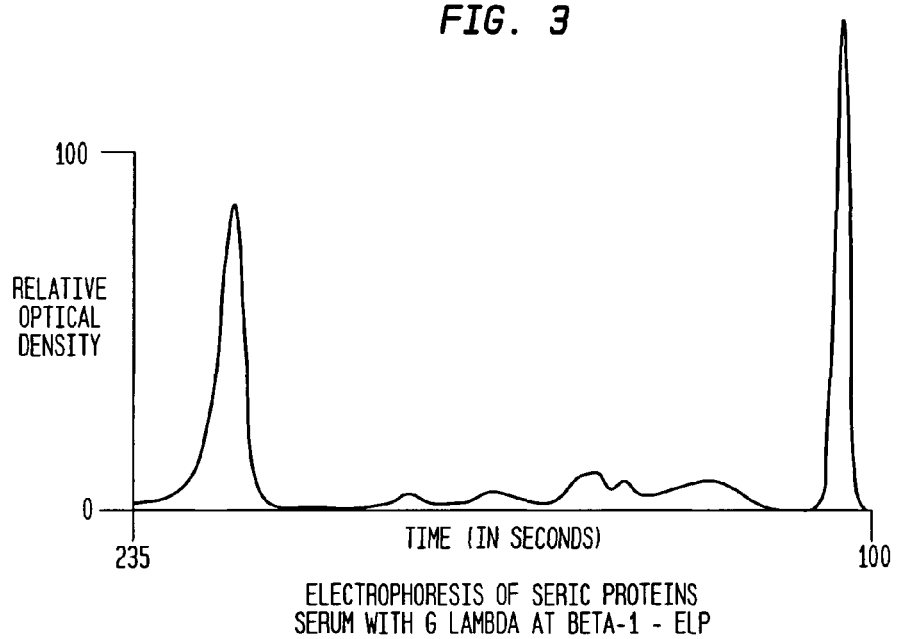
Figure 3A:
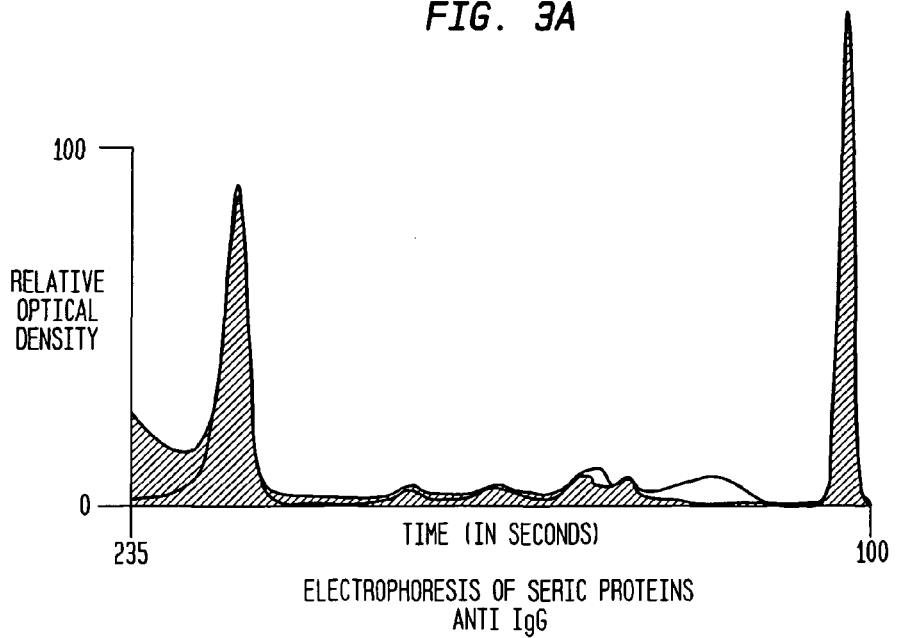
FIG. 3a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 3D:
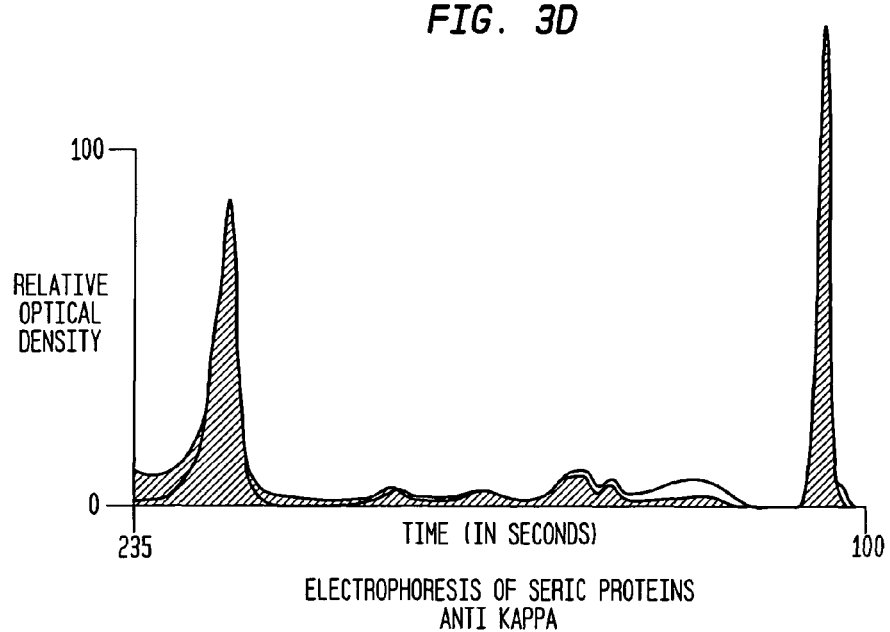
FIG. 3d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 3E:
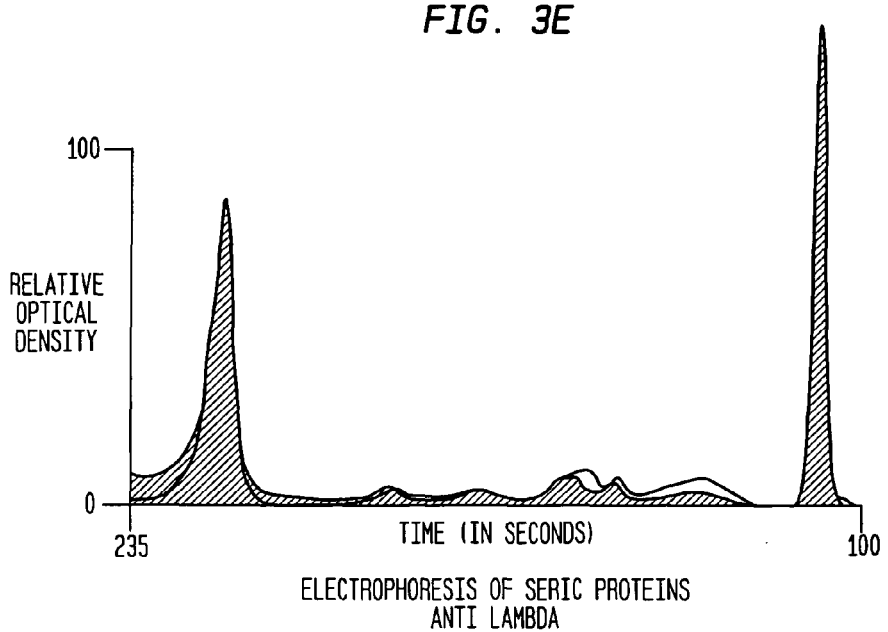
FIG. 3e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elP)".

Immunotyping of a serum containing a monoclonal type G lambda protein migrating to beta-1 on CAPILLARYS® with Sebia CAPILLARYS® B1B2+ buffer (acquisition window 100-235 s): 6 aliquots of this serum were mixed with 5 antibodies modified with 1,2,4-benzenetricarboxylic anhydride (anti-IgG, -IgA, -IgM, -kappa, -lambda) and with the medium for said antibodies (no antibodies: ELP track). Comparison with the ELP track (in black; FIG. 3) clearly shows the disappearance of the monoclonal peak at beta-1 for the aliquots treated with anti-IgG and anti-lambda. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 4

Figure 4:
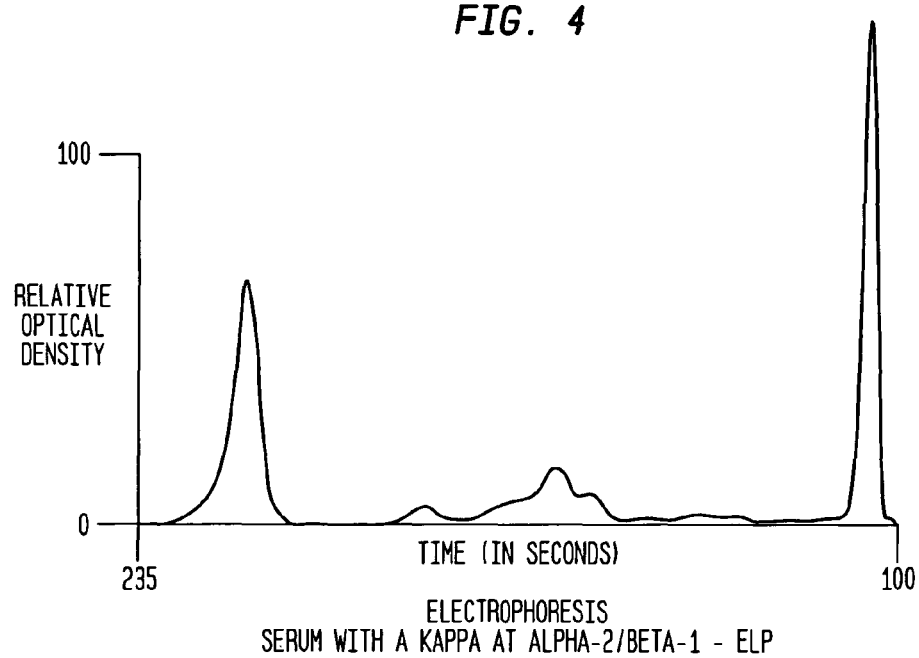
Figure 4A:
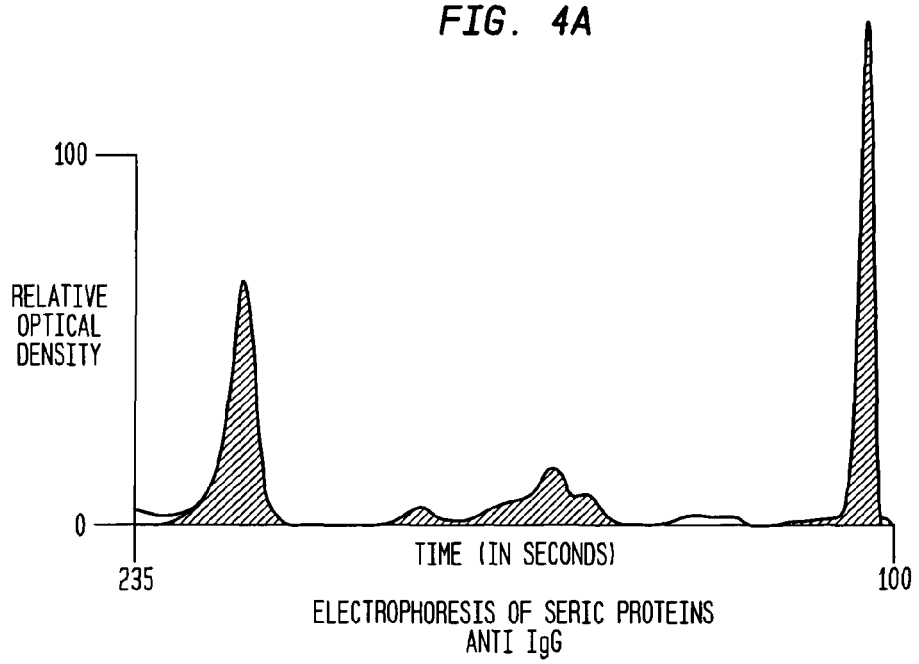
FIG. 4a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elP)".
Figure 4B:
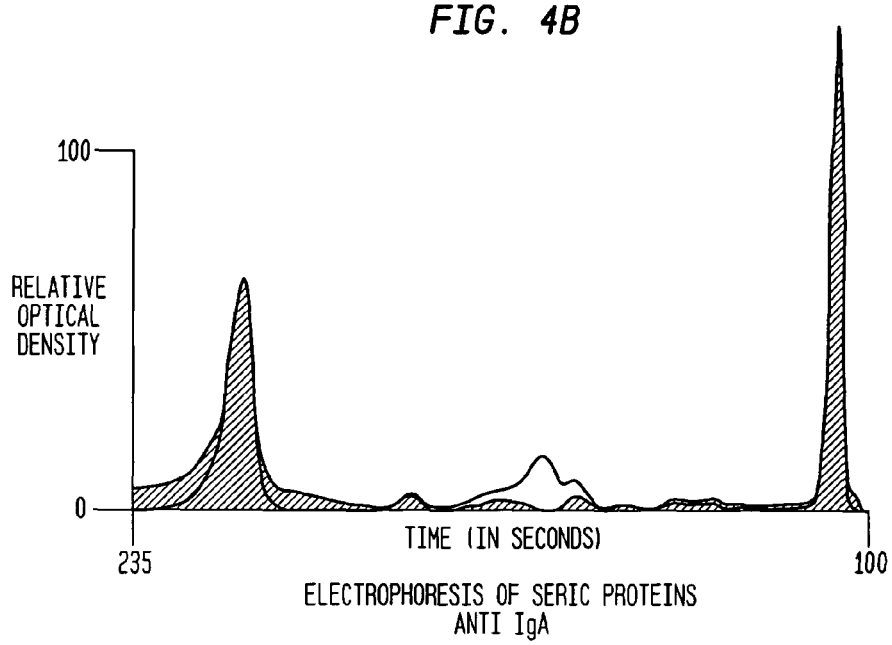
FIG. 4b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 4C:
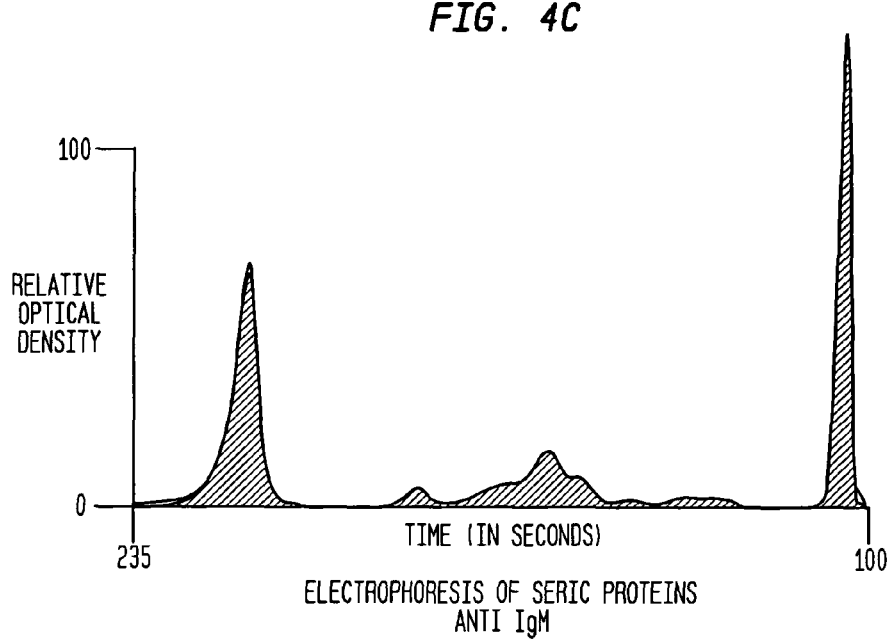
FIG. 4c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 4D:
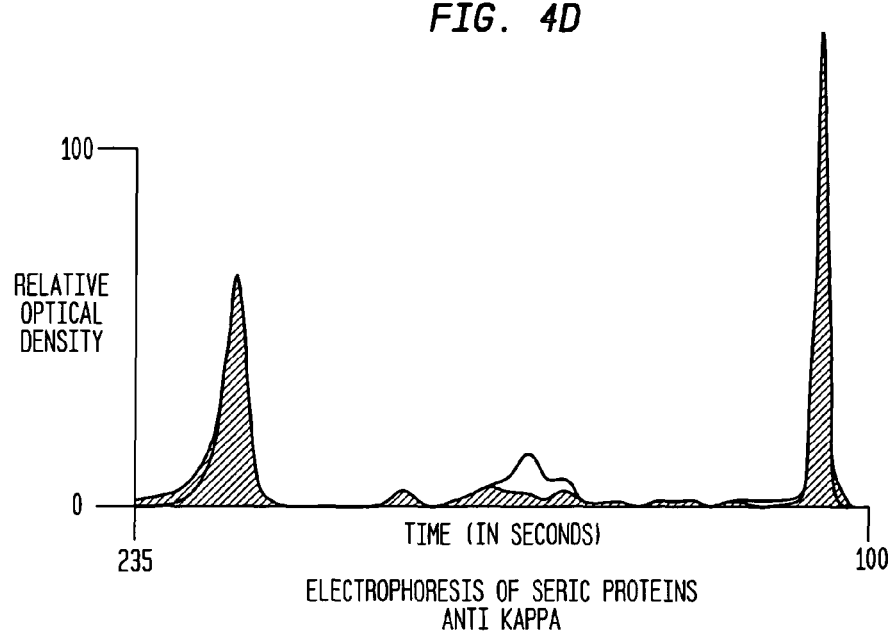
FIG. 4d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 4E:
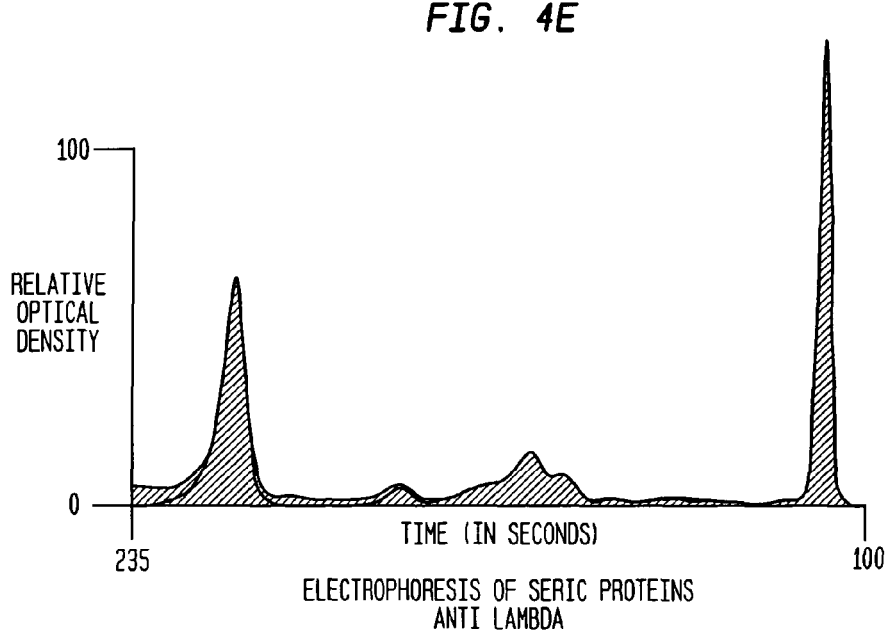
FIG. 4e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line"(elp)".

Immunotyping of a serum containing a monoclonal type A kappa protein migrating between beta-1 and alpha-2 on CAPILLARYS® with Sebia CAPILLARYS® B1B2+ buffer (acquisition window 100-235 s): 6 aliquots of this serum were mixed with 5 antibodies modified with 1,2,4-benzenetricarboxylic anhydride (anti-IgG, -IgA, -IgM, -kappa, -lambda) and with the medium for said antibodies (no antibodies: ELP track). Comparison with the ELP track (in black; FIG. 4) clearly shows the disappearance of the monoclonal peak at beta-1/alpha-2 for the aliquots treated with anti-IgA and anti-kappa. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 5

Figure 5:
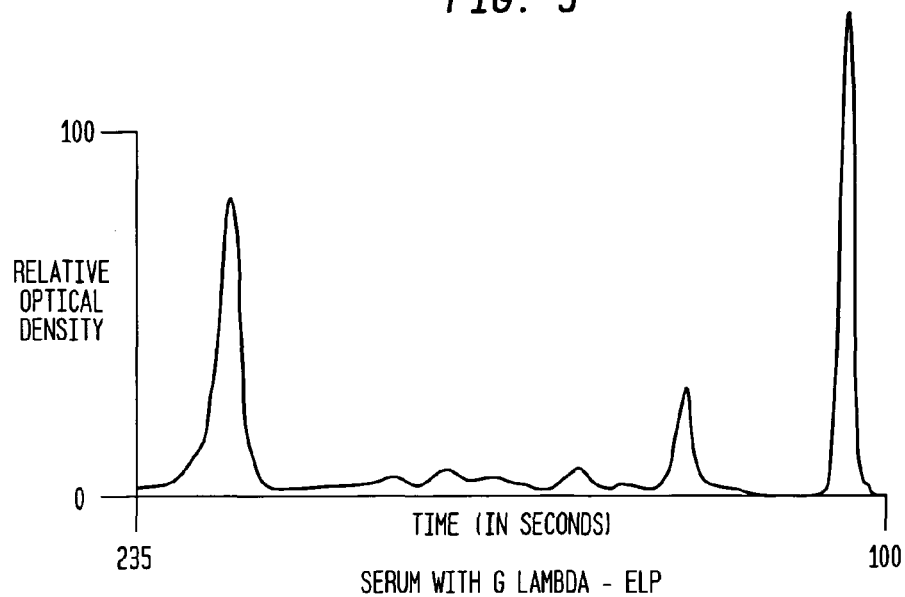
Figure 5A:
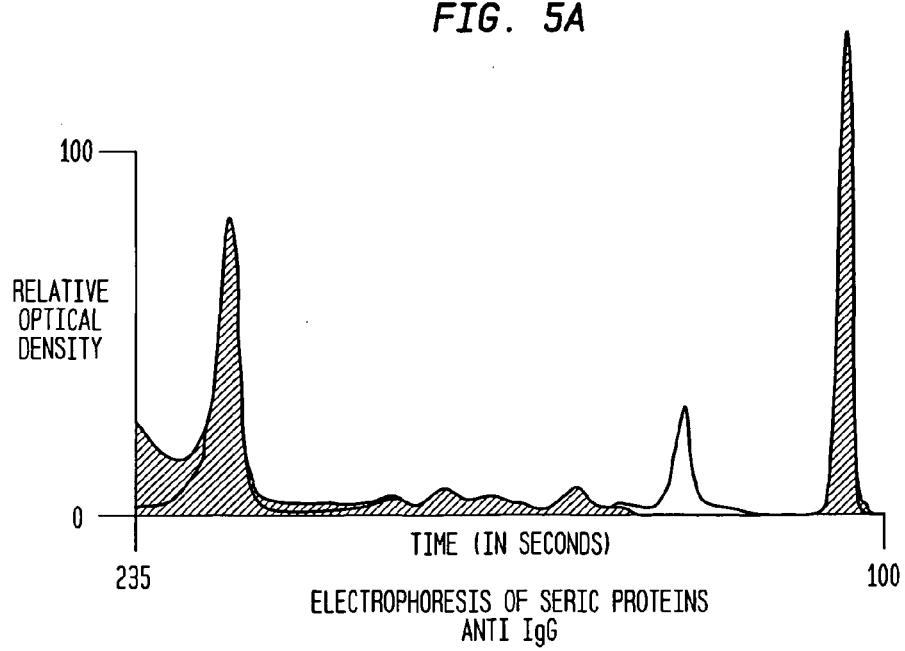
FIG. 5a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 5B:
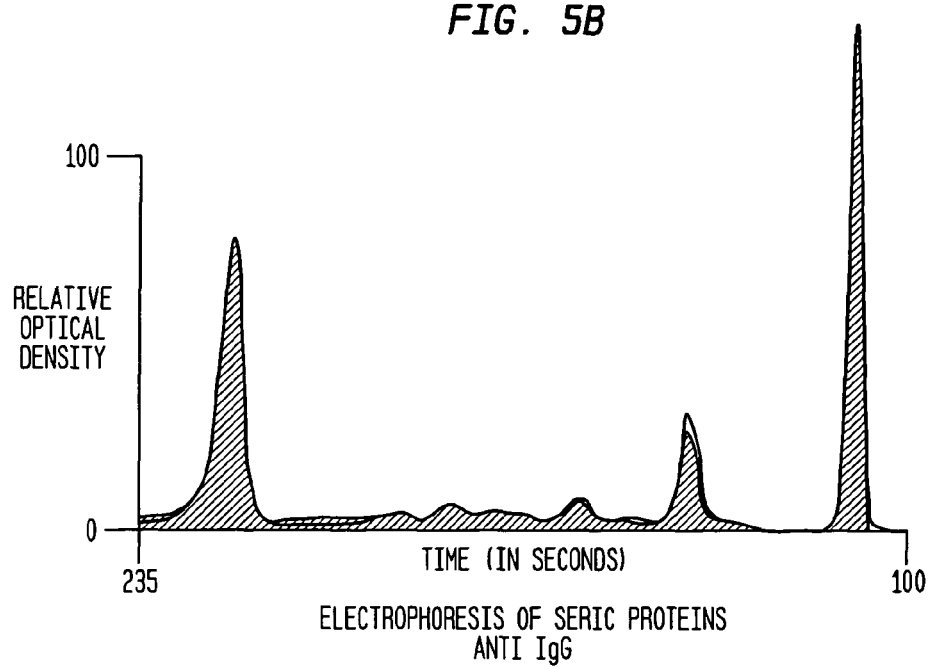
FIG. 5b is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 5C:
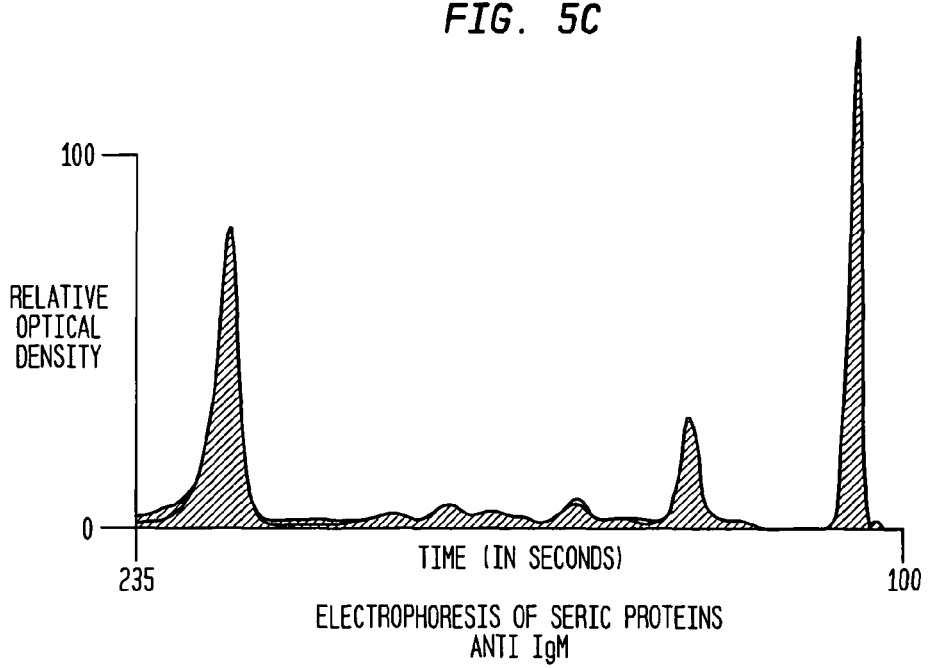
FIG. 5c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 5D:
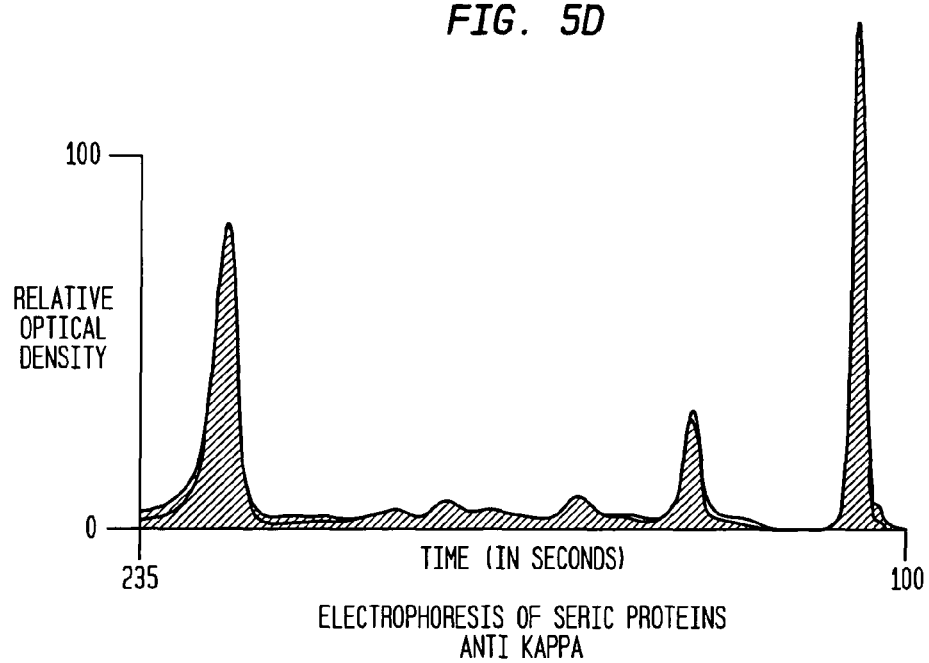
FIG. 5d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 5E:
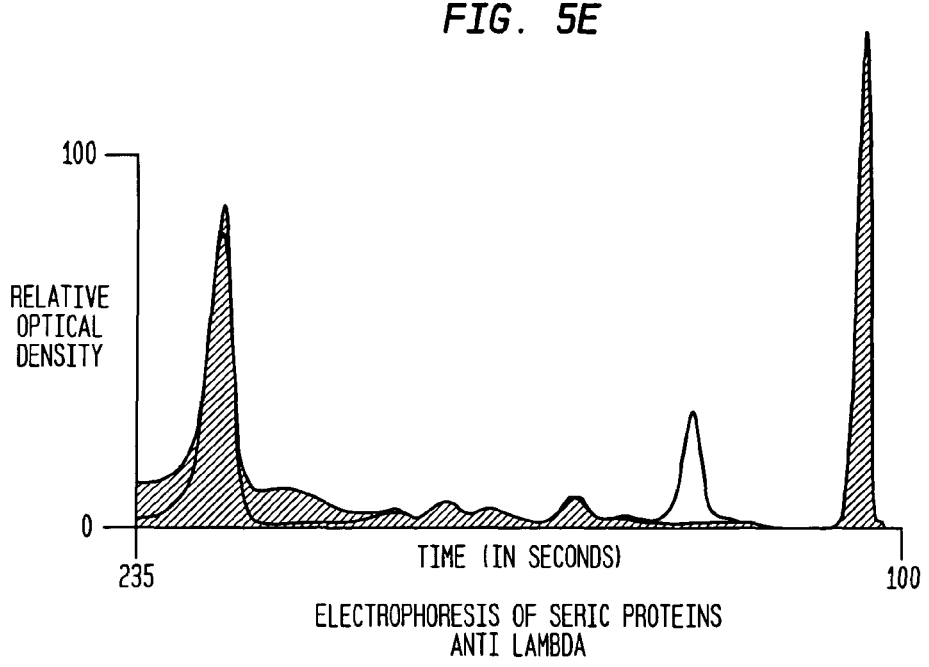
FIG. 5e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

Immunotyping of a serum containing a monoclonal type G lambda protein migrating to gamma on CAPILLARYS® with Sebia CAPILLARYS® B1B2+ buffer (acquisition window 100-235 s): 6 aliquots of this serum were mixed with 5 antibodies modified with 1,2,4-benzenetricarboxylic anhydride (anti-IgG, -IgA, -IgM, -kappa, -lambda) and with the medium for said antibodies (no antibodies: ELP track). Comparison with the ELP track (in black; FIG. 5) clearly shows the disappearance of the monoclonal peak at gamma for the aliquots treated with anti-IgG and anti-lambda. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 6

Figure 6:
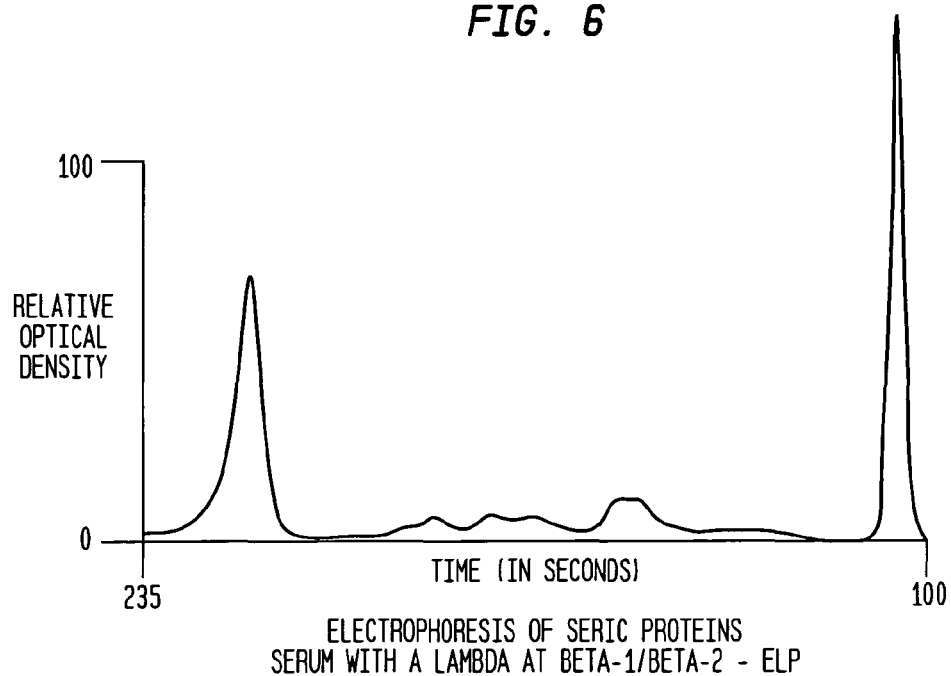
Figure 6A:
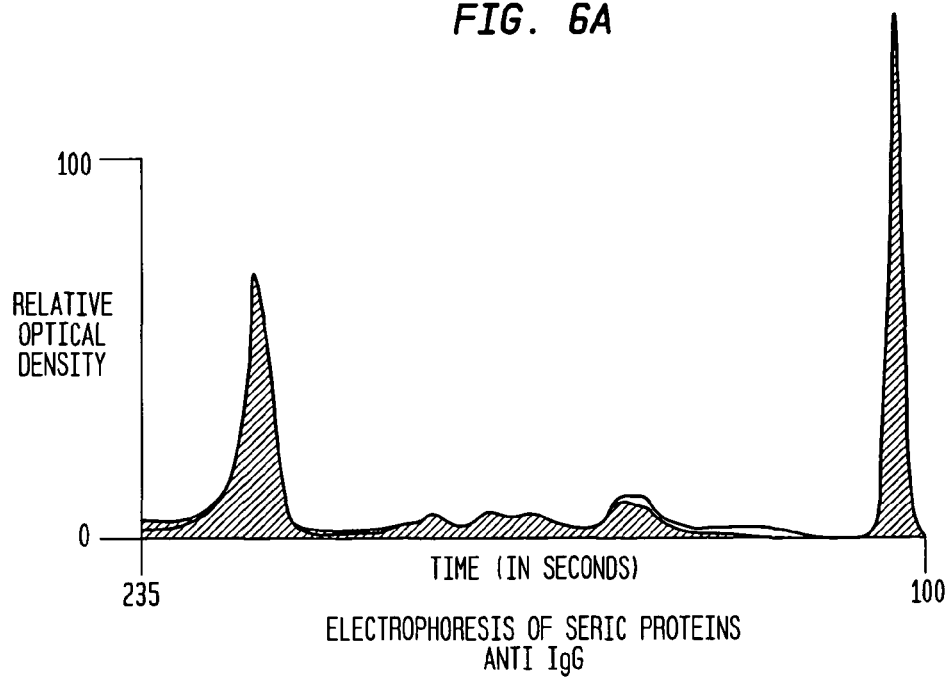
FIG. 6a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 6B:
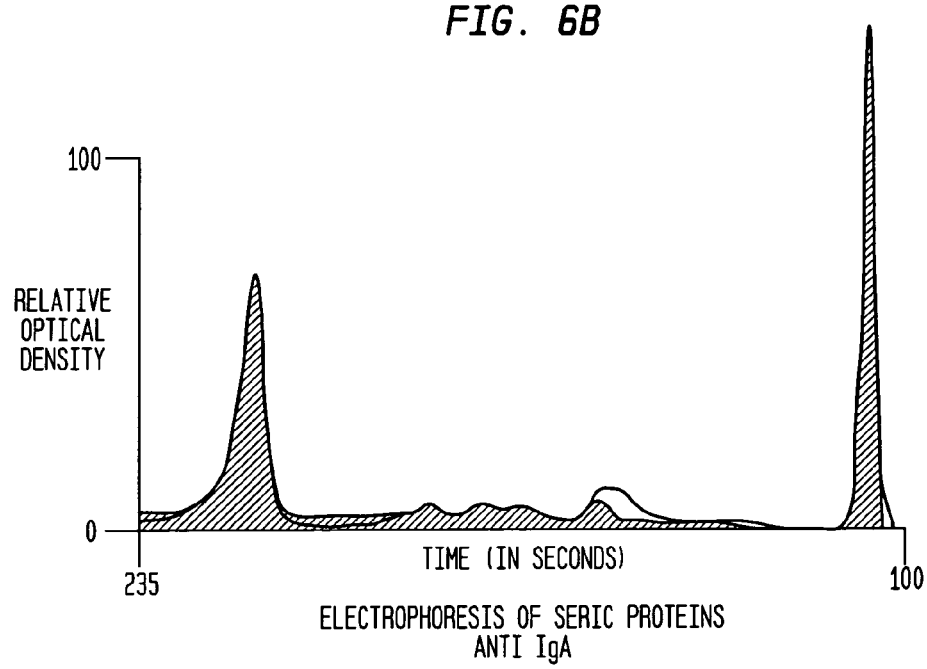
FIG. 6b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 6C:
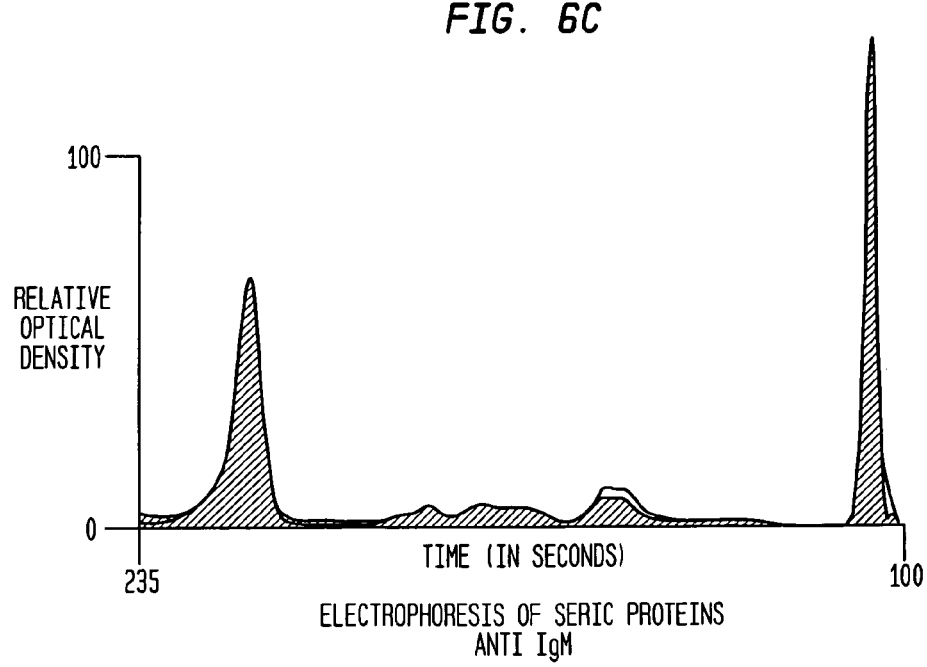
FIG. 6c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 6D:
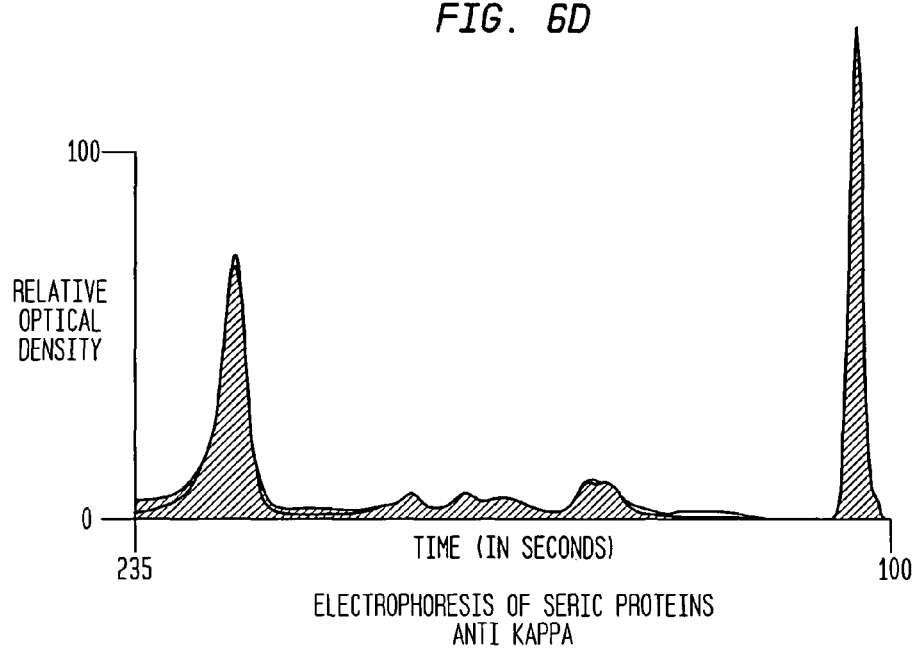
FIG. 6d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 6E:
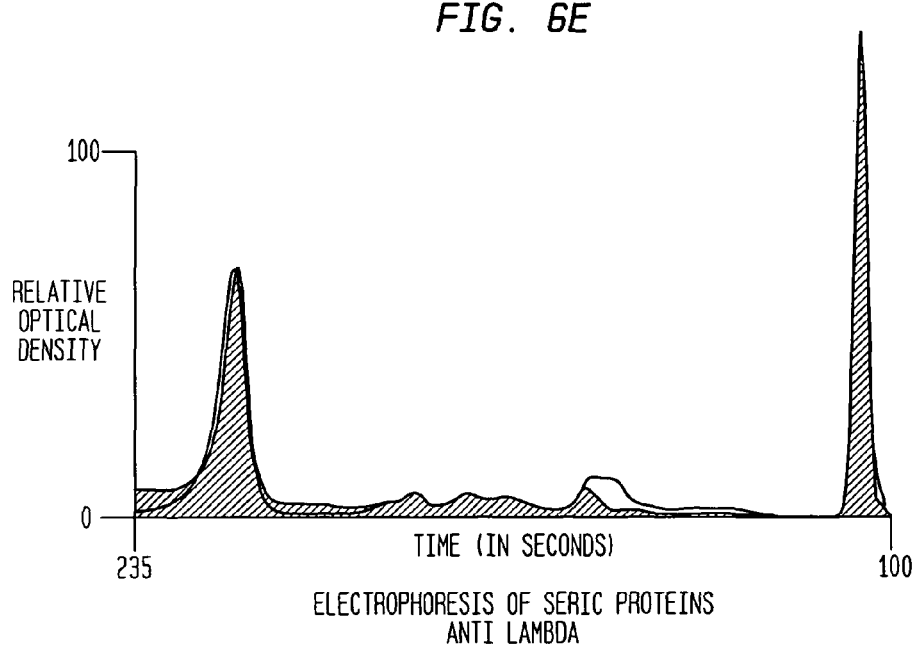
FIG. 6e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

Immunotyping of a serum containing a monoclonal type A lambda protein migrating between beta-1 and beta-2 on CAPILLARYS® with Sebia CAPILLARYS® B1B2+ buffer (acquisition window 100-235 s): 6 aliquots of this serum were mixed with 5 antibodies modified with 1,2,4-benzenetricarboxylic anhydride (anti-IgG, -IgA, -IgM, -kappa, -lambda) and with the medium for said antibodies (no antibodies: ELP track). Comparison with the ELP track (in black; FIG. 6) clearly shows the disappearance of the monoclonal peak at beta-1/beta-2 for the aliquots treated with anti-IgA and anti-lambda. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 7

Figure 7:
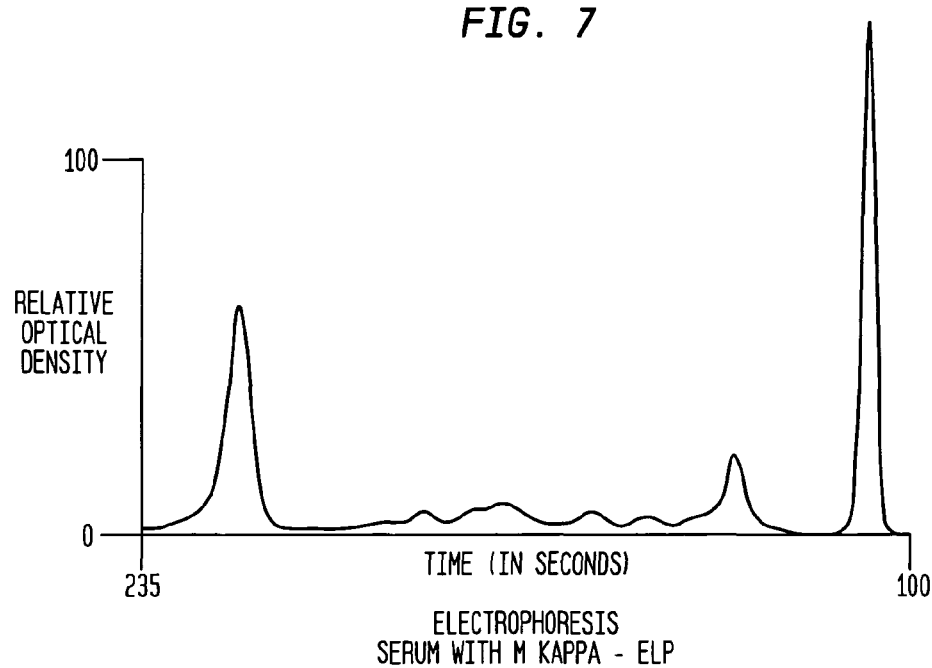
Figure 7A:
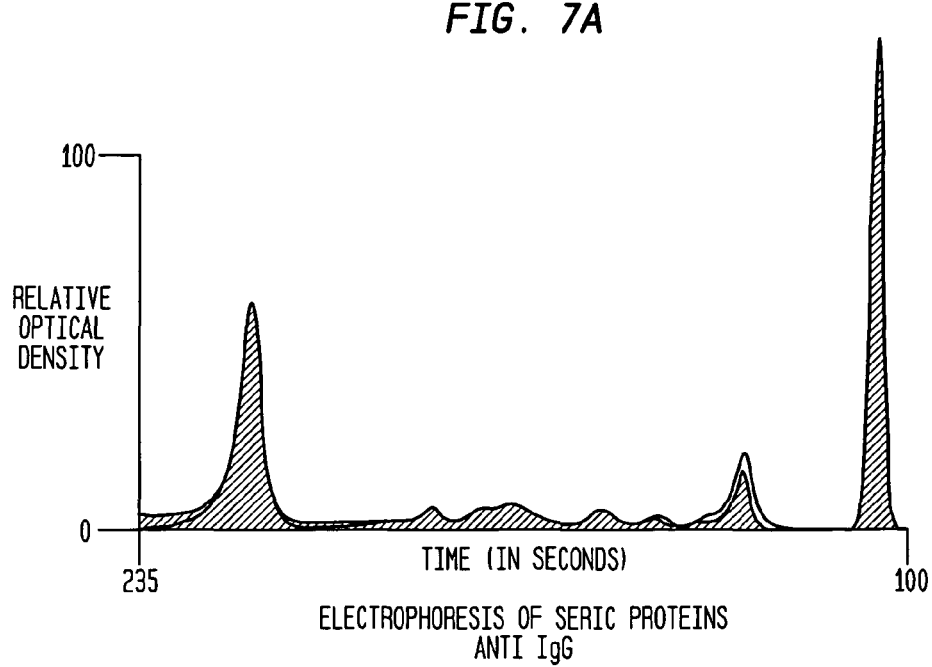
FIG. 7a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 7B:
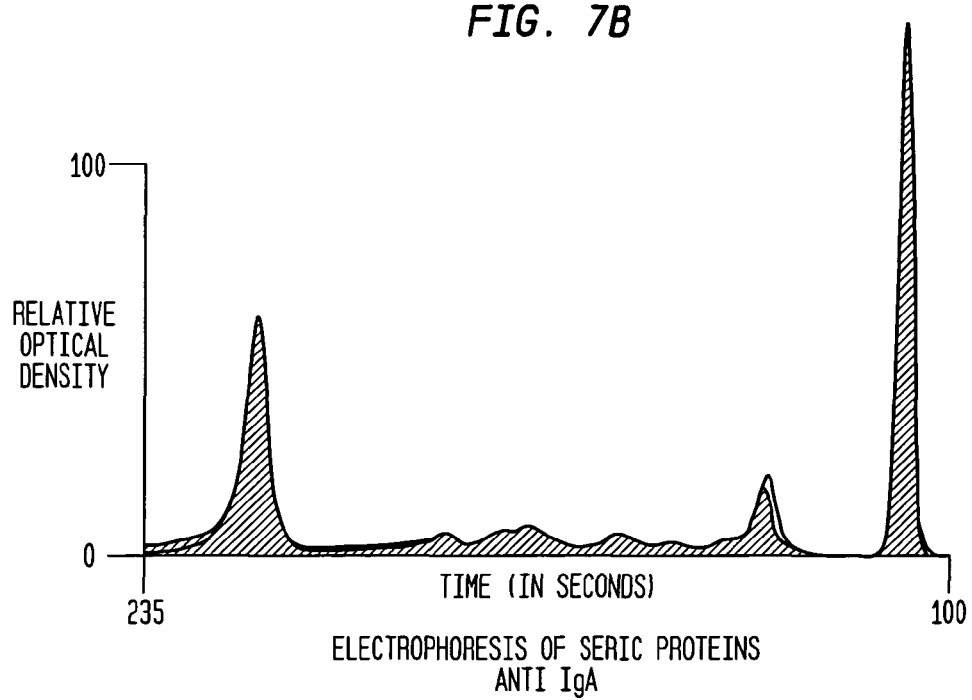
FIG. 7b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 7C:
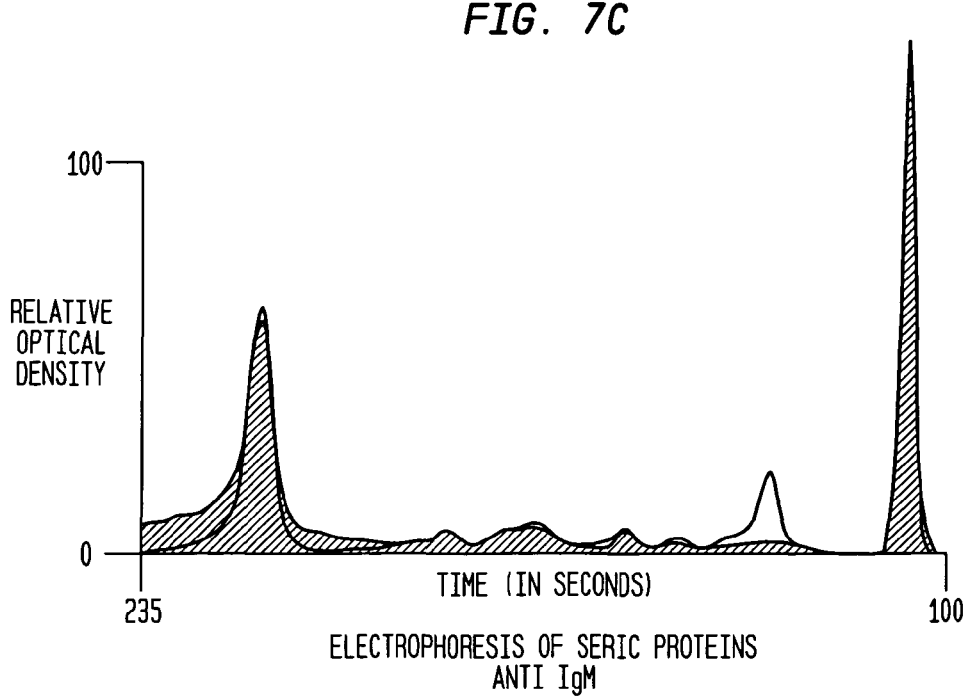
FIG. 7c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 7D:
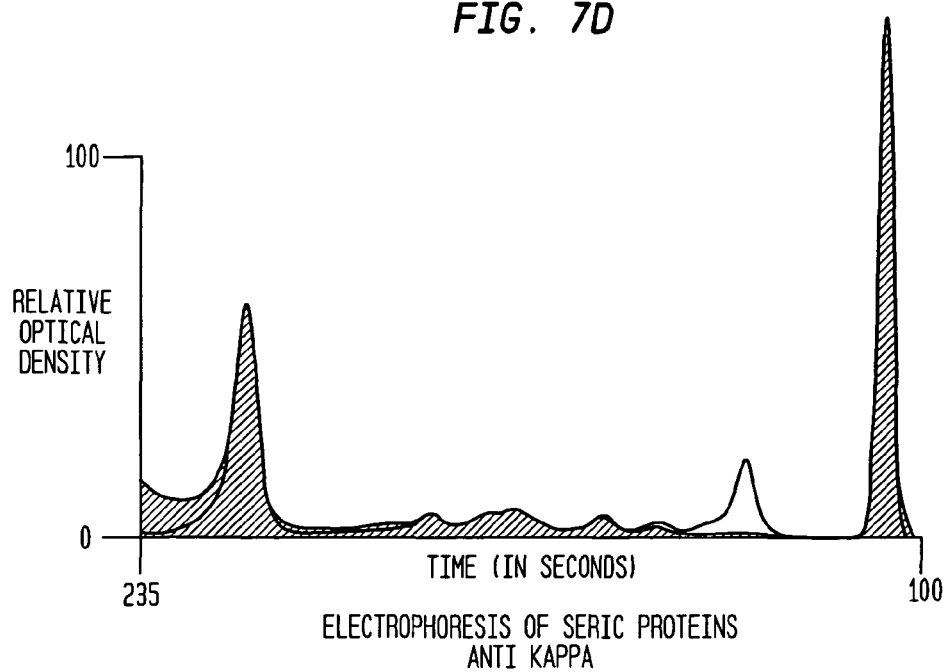
FIG. 7d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 7E:
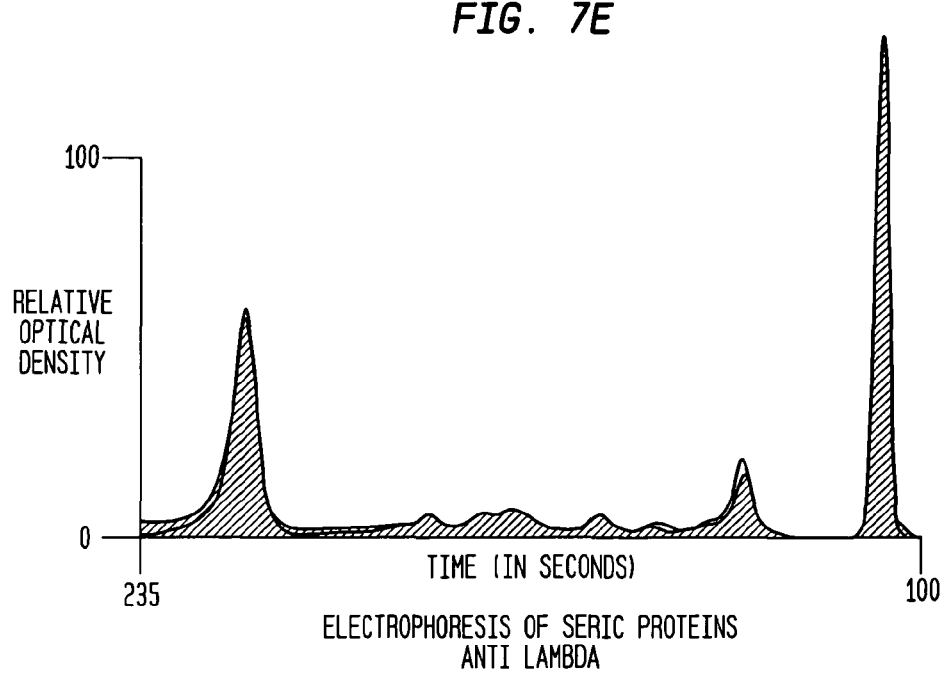
FIG. 7e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

Immunotyping of a serum containing a monoclonal type M kappa protein migrating to gamma on CAPILLARYS® with Sebia CAPILLARYS® B1B2+ buffer (acquisition window 100-235 s): 6 aliquots of this serum were mixed with 5 antibodies modified with 1,2,4-benzenetricarboxylic anhydride (anti-IgG, -IgA, -IgM, -kappa, -lambda) and with the medium for said antibodies (no antibodies: ELP track). Comparison with the ELP track (in black; FIG. 7) clearly shows the disappearance of the monoclonal peak at gamma for the aliquots treated with anti-IgM and anti-kappa. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 8

Figure 8:
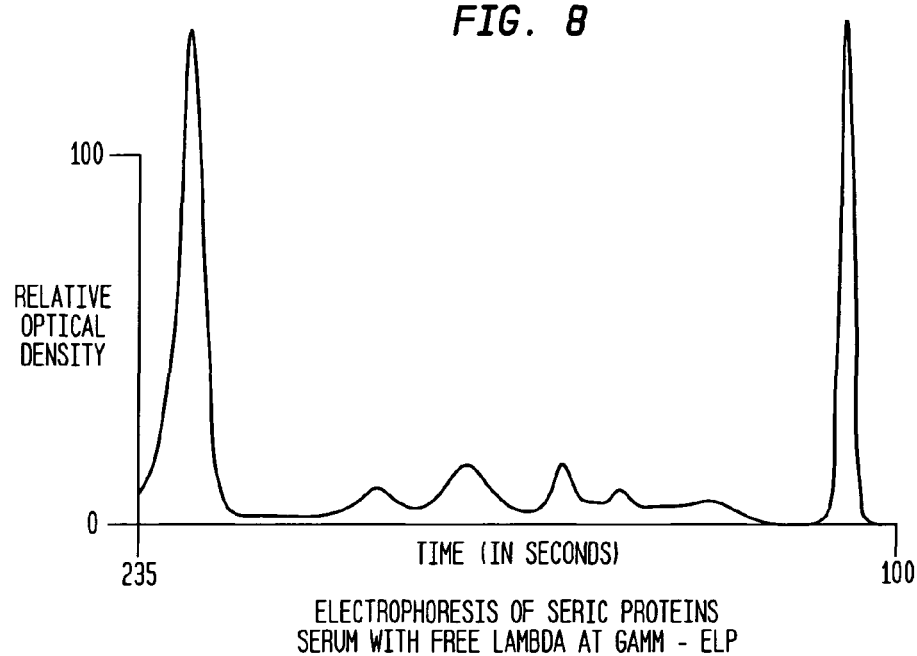
Figure 8A:
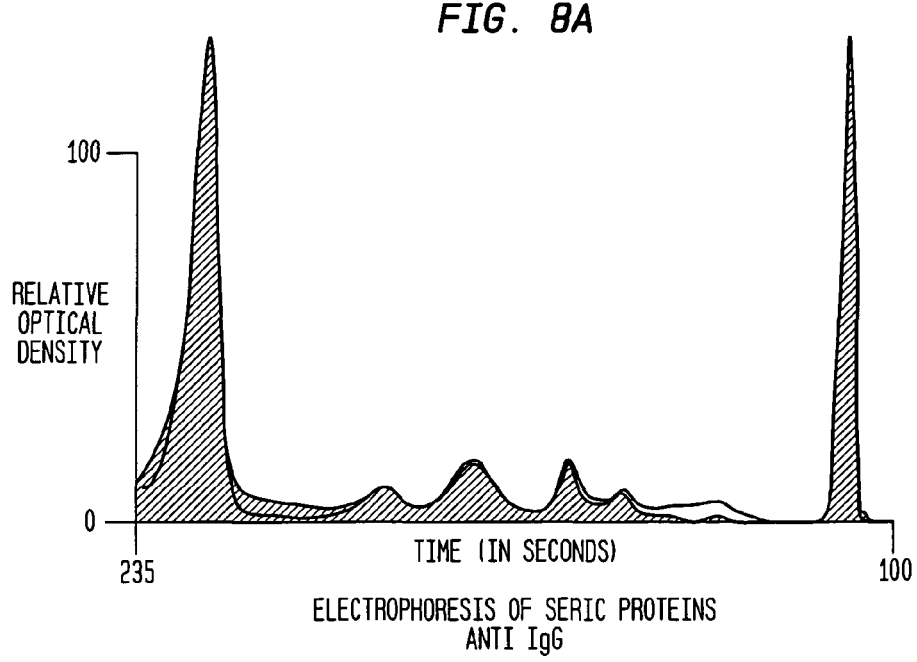
FIG. 8a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 8B:
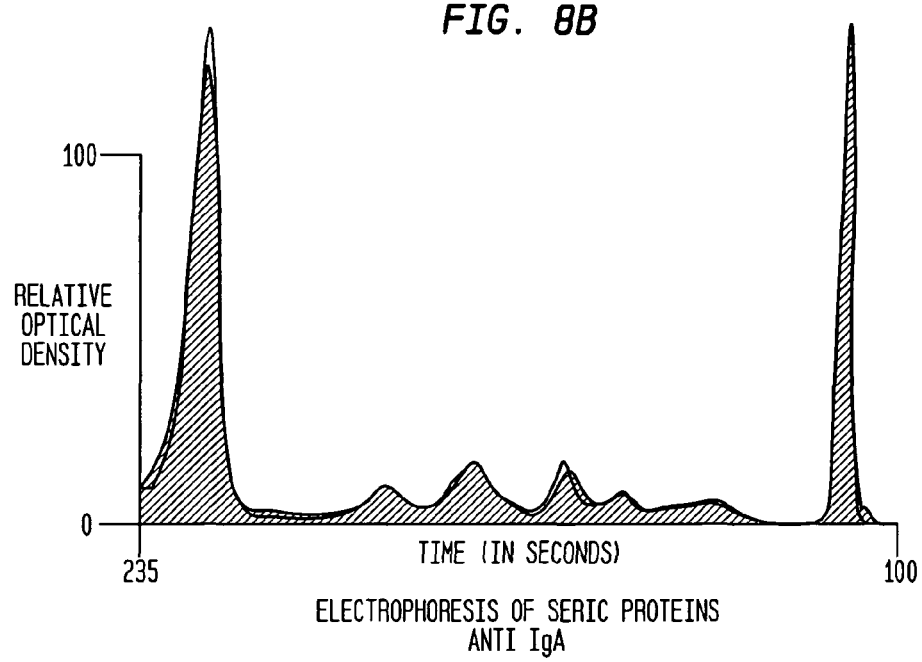
FIG. 8b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 8C:
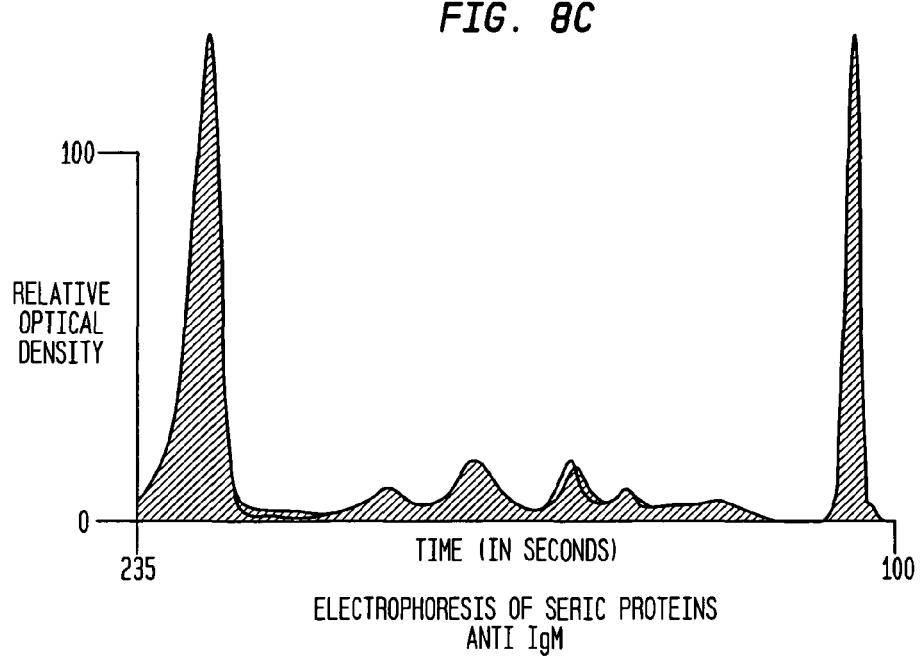
FIG. 8c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 8D:
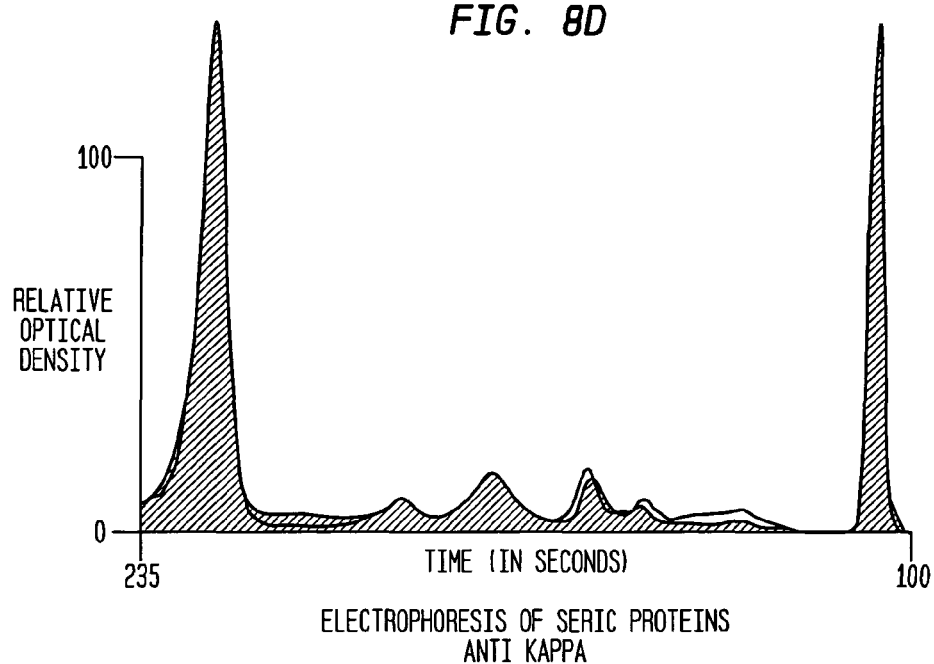
FIG. 8d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 8E:
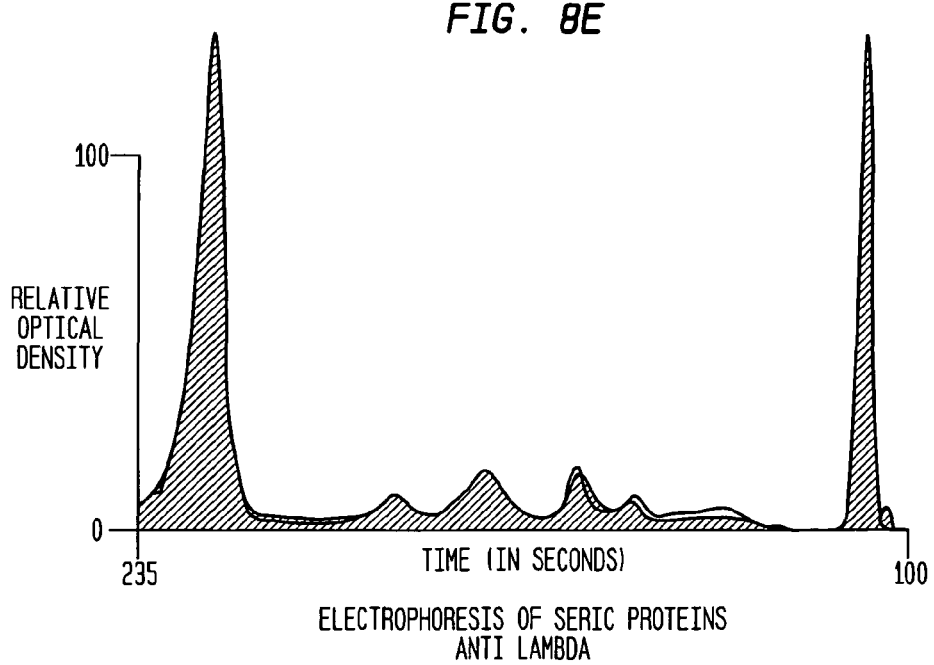
FIG. 8e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

Immunotyping of a serum containing a monoclonal free lambda type protein migrating to gamma on CAPILLARYS® with Sebia CAPILLARYS® B1B2+ buffer (acquisition window 100-235 s): 8 aliquots of this serum were mixed with 7 antibodies modified with 1,2,4-benzenetricarboxylic anhydride (anti-IgG, -IgA, -IgM, -kappa, -lambda, -free kappa, -free lambda) and with the medium for said antibodies (no antibodies: ELP track). Comparison with the ELP track (in black; FIG. 8) clearly shows the disappearance of the monoclonal peak at gamma for the aliquots treated with anti-lambda and anti-free lambda. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 9

Figure 9:
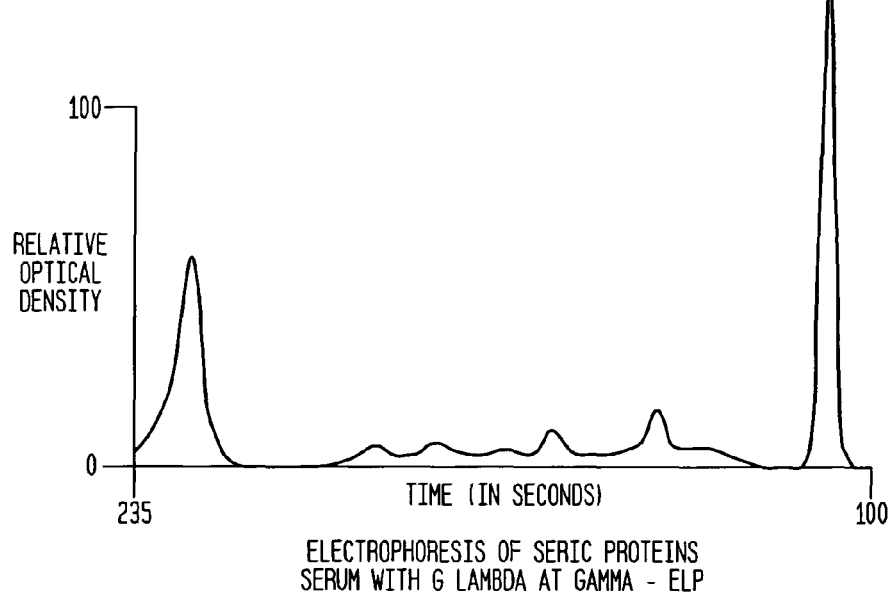
Figure 9A:
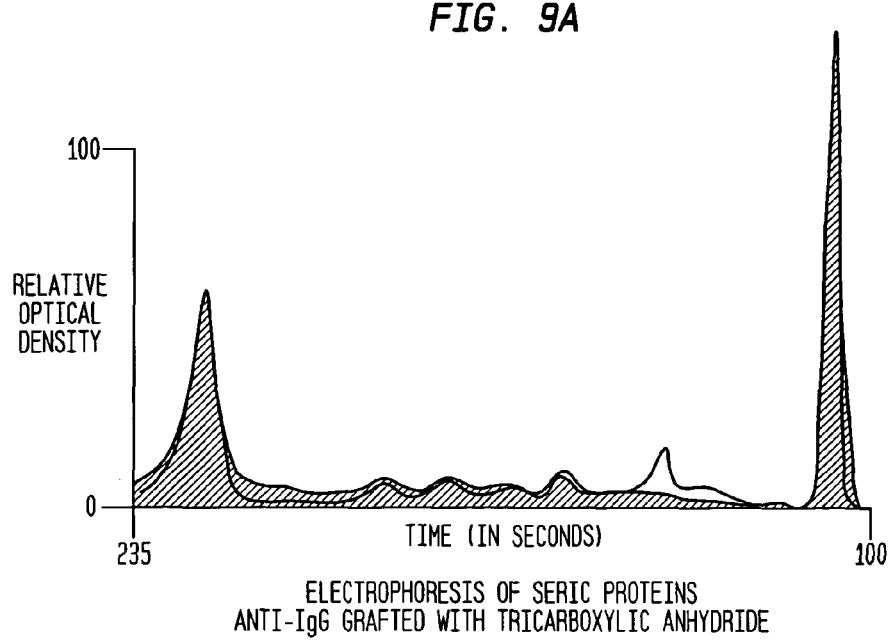
FIG. 9a is an electrophoretic profile of serum containing anti-human IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 9B:
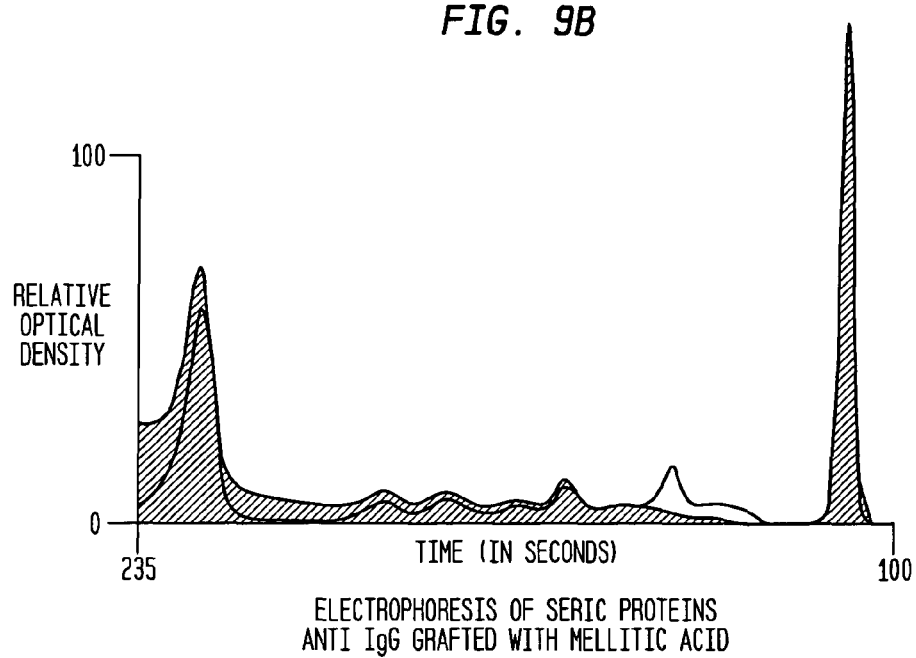
FIG. 9b is an electrophoretic profile of serum containing anti-human IgG antibodies modified with mellitic acid/EDCI. The gray surface of the profile represents seric proteins separated in the presence of the antibodies of the invention. The profile of the seric proteins separated outside the presence of the antibodies also appears, but with a fainter line "(elp)".

Comparison of immunotyping obtained with an anti-human IgG antibody modified by 1,2,4-benzenetricarboxylic anhydride or by mellitic acid/EDCI on a serum containing a monoclonal type G kappa protein migrating to gamma on CAPILLARYS® with Sebia CAPILLARYS® B1B2+ buffer (acquisition window 100-235 s): 3 aliquots of this serum were mixed with 2 anti-human IgG modified with 1,2,4-benzenetricarboxylic anhydride and with mellitic acid/EDCI and with the medium for said antibodies (no antibodies: ELP track). Comparison with the ELP track (in black; FIG. 9) clearly shows the disappearance of the monoclonal peak at beta-1 for the aliquots treated with the 2 modified antibodies. Note also for the two cases the absence of interference of the immunocomplexes and modified antibodies with the globulin migration. The peak migrating in front of the gammas is an injection marker to facilitate superimposition of the profiles.

Example 10

Figure 10:
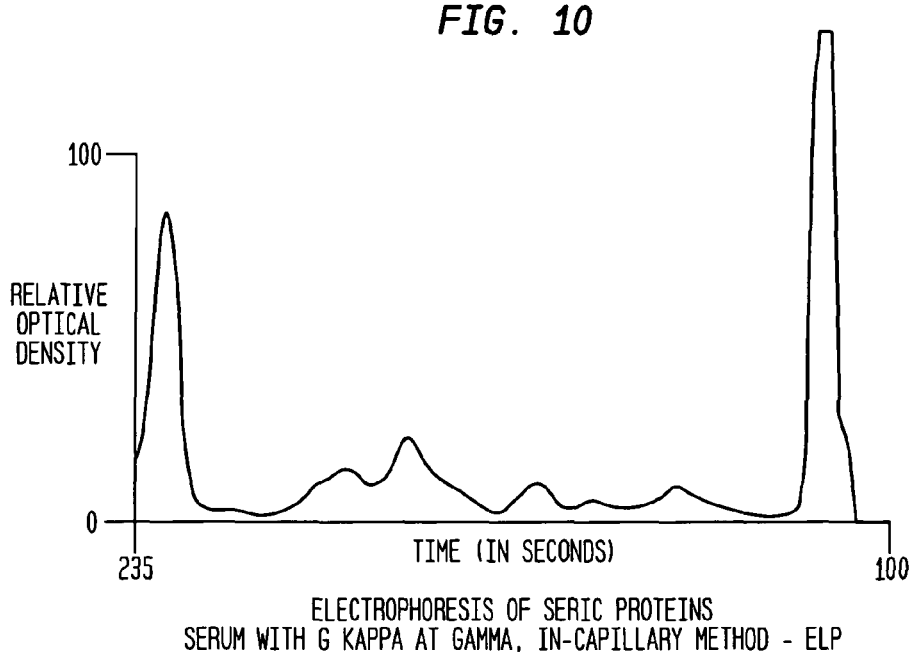
Figure 10C:
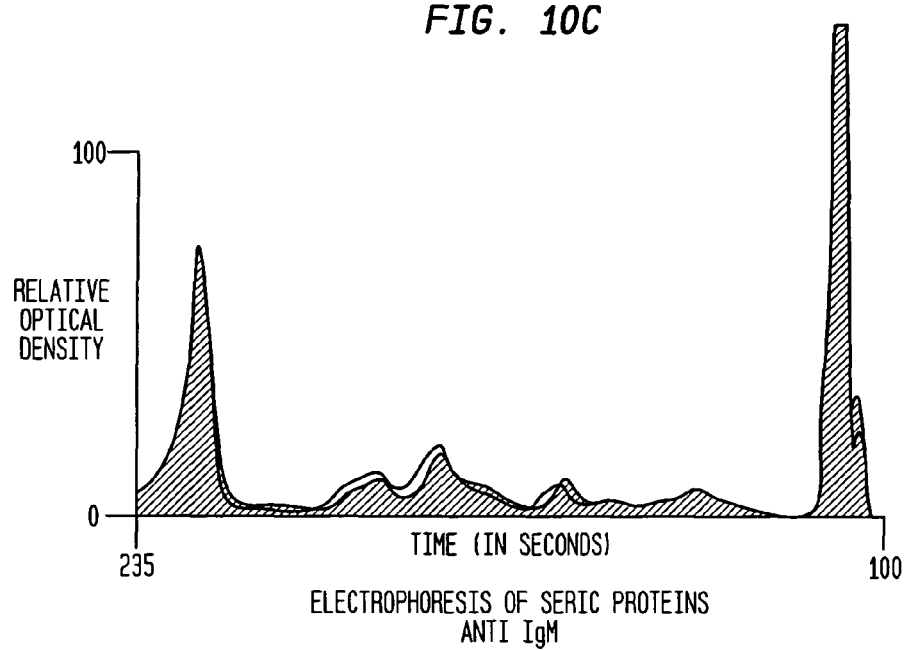
FIG. 10c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 10D:
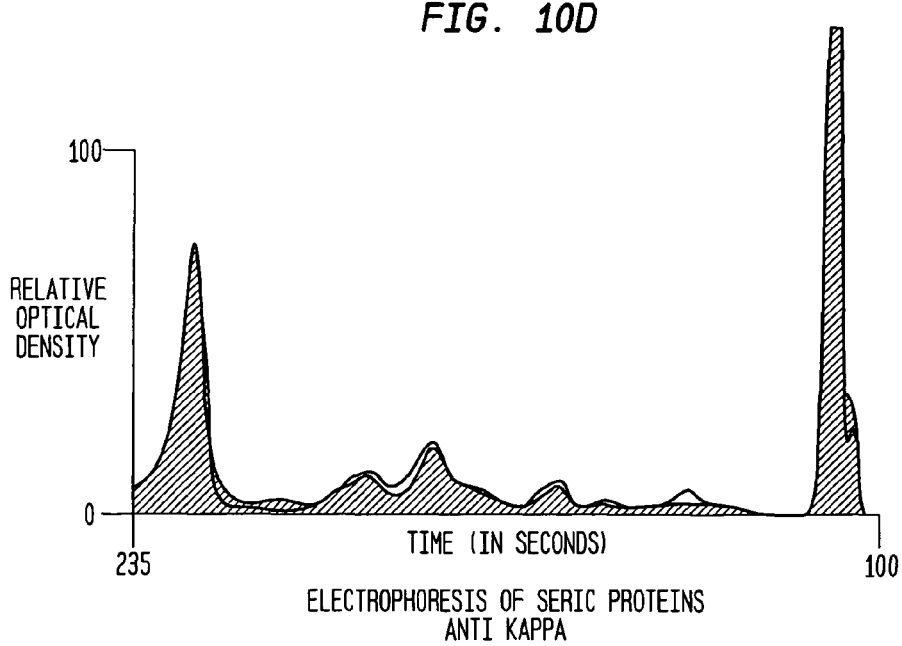
FIG. 10d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 10E:
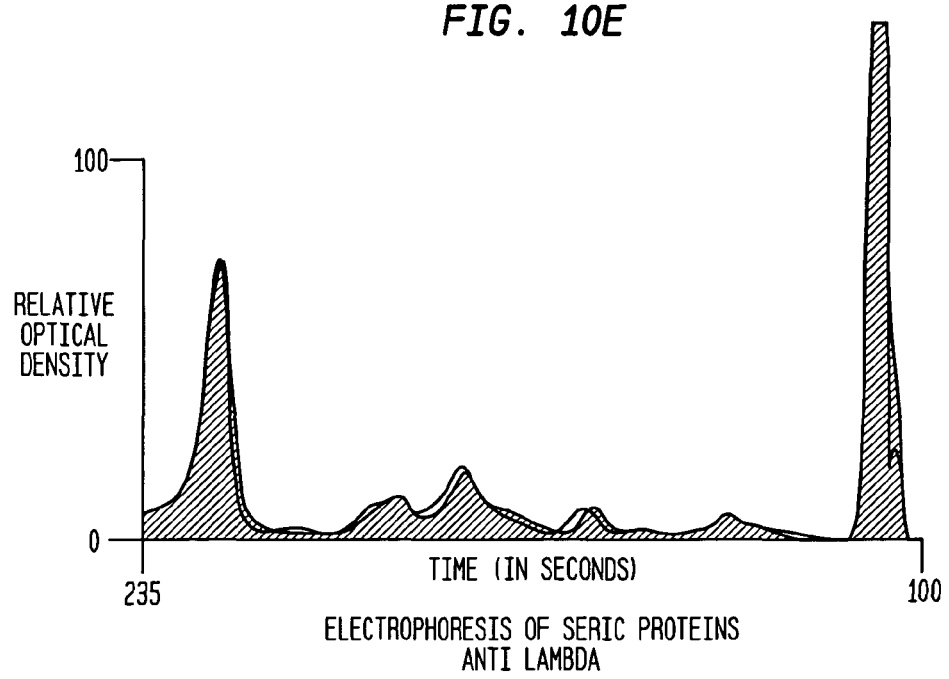
FIG. 10e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

In-capillary immunotyping of a serum containing a monoclonal type G kappa protein migrating to gamma on CAPILLARYS® with Sebia CAPILLARYS® B1B2+ buffer (acquisition window 100-235 s): the antibody medium (no antibodies) and 5 antibodies modified with 1,2,4-benzenetricarboxylic anhydride (anti-IgG, -IgA, -IgM, -kappa, -lambda) were placed in a first head, 6 aliquots of this serum were diluted in Sebia CAPILLARYS® B1B2+ buffer containing the injection marker (head 2). The antibodies then the diluted serum aliquots were injected and the 6 migrations were carried out. Comparison with the ELP track (in black; FIG. 10) clearly shows the disappearance of the monoclonal peak at gamma for the aliquots treated with anti-IgG and anti-kappa. For the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

Example 11

Figure 11:
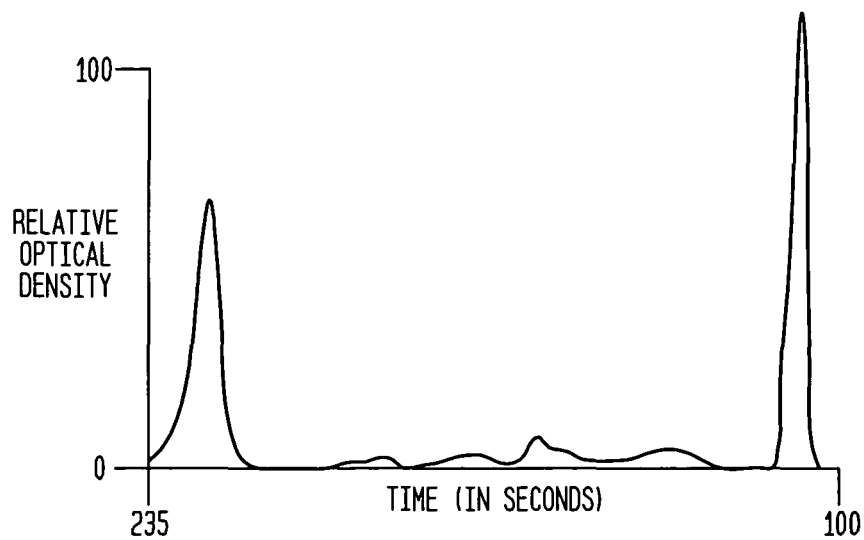
Figure 11A:
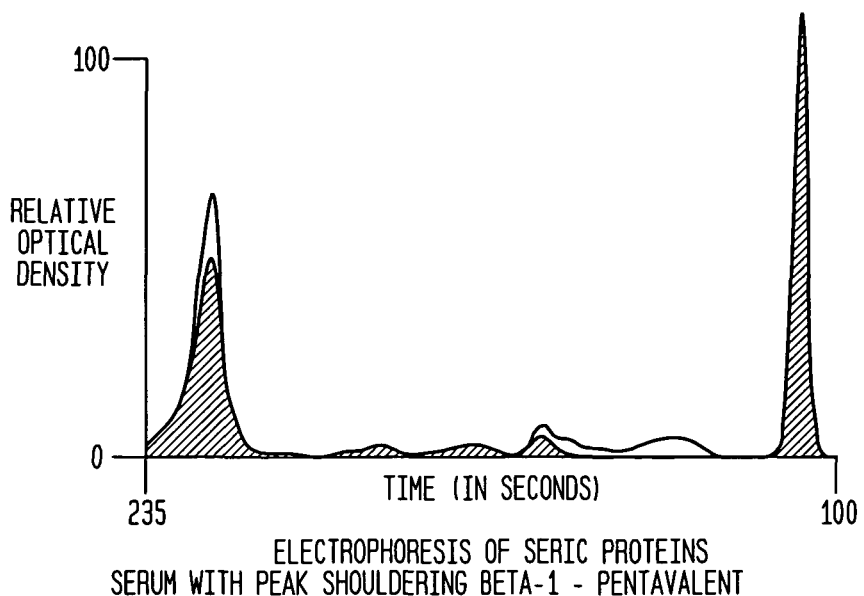
FIG. 11a is an electrophoretic profile of pentavalent serum, which is a mixture of anti-IgG, -IgA, -IgM, -kappa and -lambda modified with 1,2,4-benzenetricarboxylic acid anhydride shouldering a peak at beta-1 on Capillarys. The gray surface of the profile represents seric proteins separated in the presence of the antibodies of the invention. The profile of the seric proteins separated outside the presence of the antibodies also appears, but with a fainter line "(elp)".

Use of pentavalent antiserum (mixture of anti-IgG, -IgA, -IgM, -kappa and -lambda modified by 1,2,4-benzenetricarboxylic anhydride) to verify the Mc nature of a peak shouldering beta-1 in a serum by analysis on the CAPILLARYS® apparatus with a Sebia CAPILLARYS® B1B2+ buffer (acquisition window: 100-235 s): 2 aliquots of this serum were mixed with pentavalent antiserum and with the medium for these antibodies (no antibodies: ELP track). Comparison with the ELP track (in black; FIG. 11) clearly shows the disappearance of the peak shouldering beta-1 for the track treated with pentavalent antiserum, indicating the Mc nature of this peak (type M kappa Mc protein). Note also the disappearance of the polyclonal background, the absence of beta-2 fraction for this serum and the absence of interference of immunocomplexes and modified antibodies with the globulin migration. The peak migrating in front of the gammas is an injection marker to facilitate superimposition of the profiles.

Example 12

Figure 12:
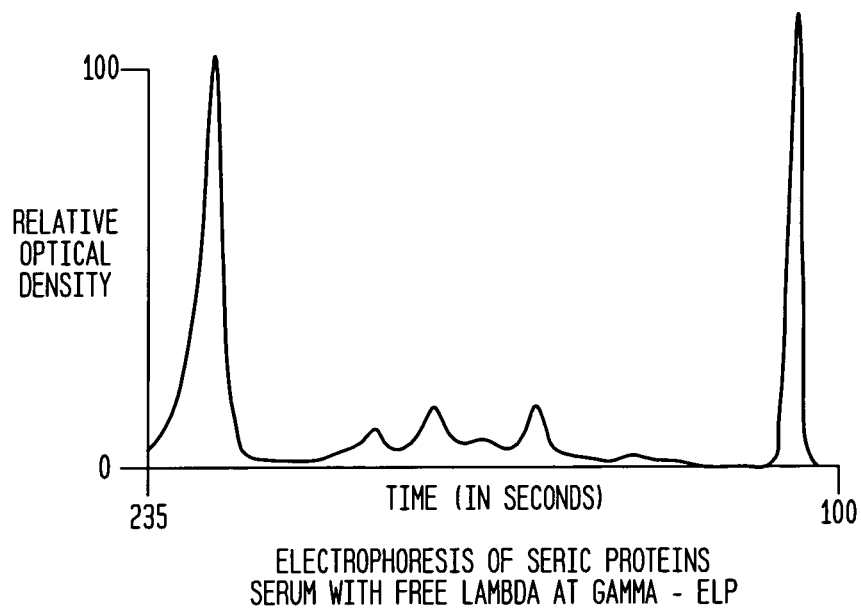
Figure 12A:
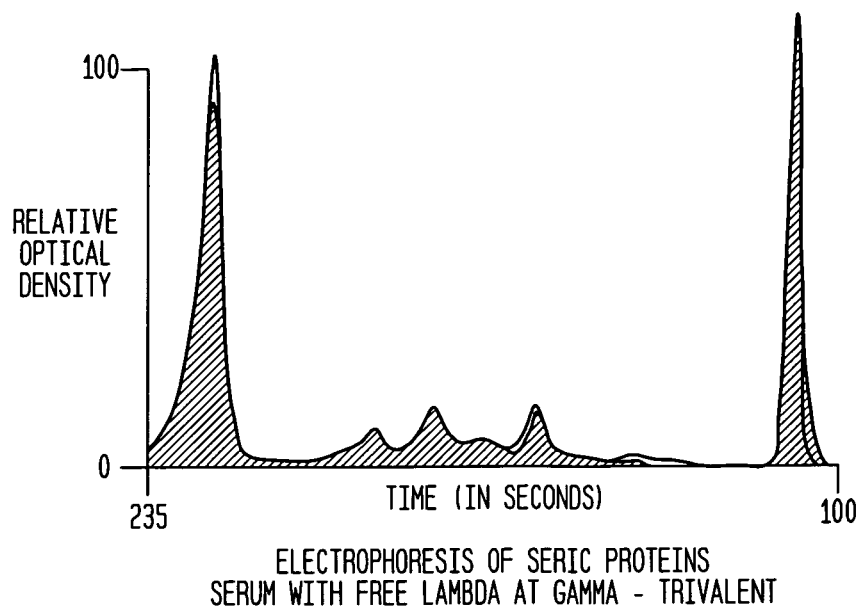
FIG. 12a is an electrophoretic profile of trivalent serum, which is a mixture of anti-IgG, -IgA, -IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 12B:
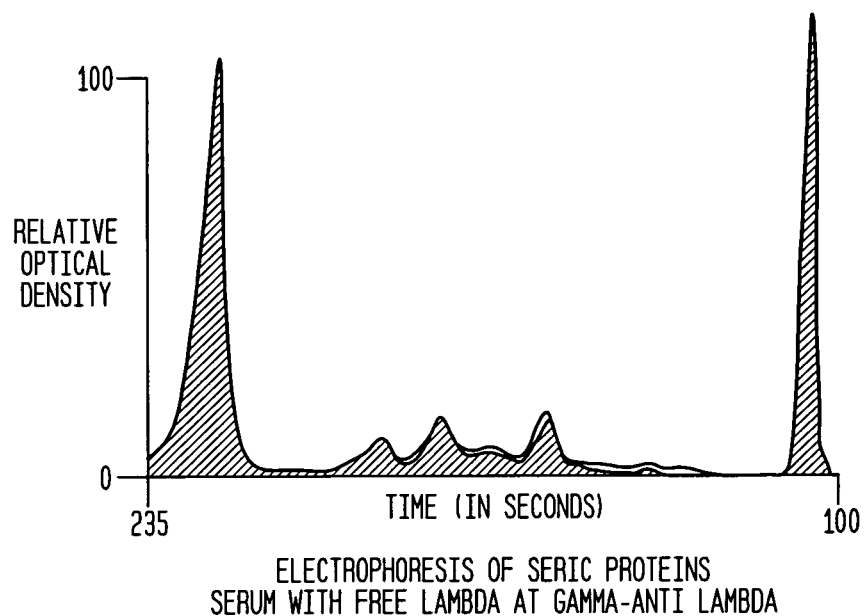
FIG. 12b is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 12C:
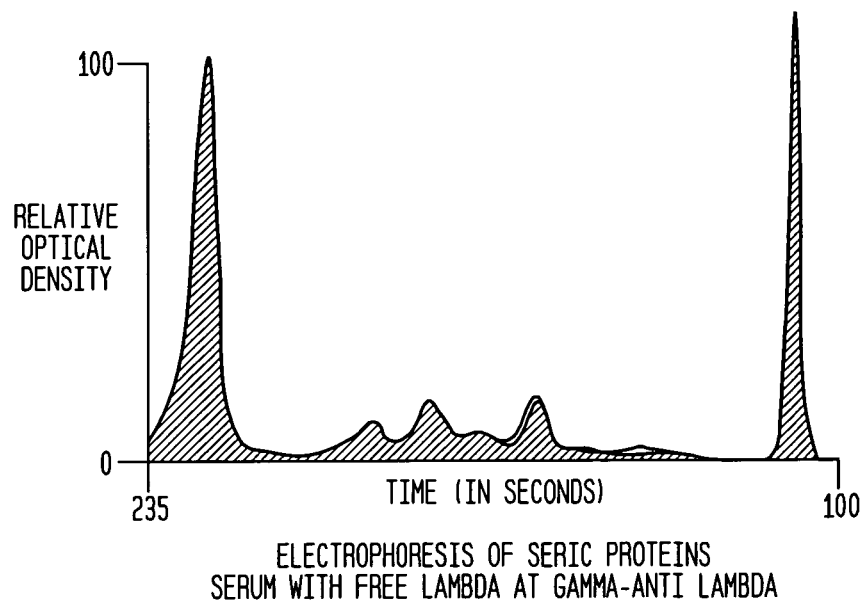
FIG. 12c is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 12D:
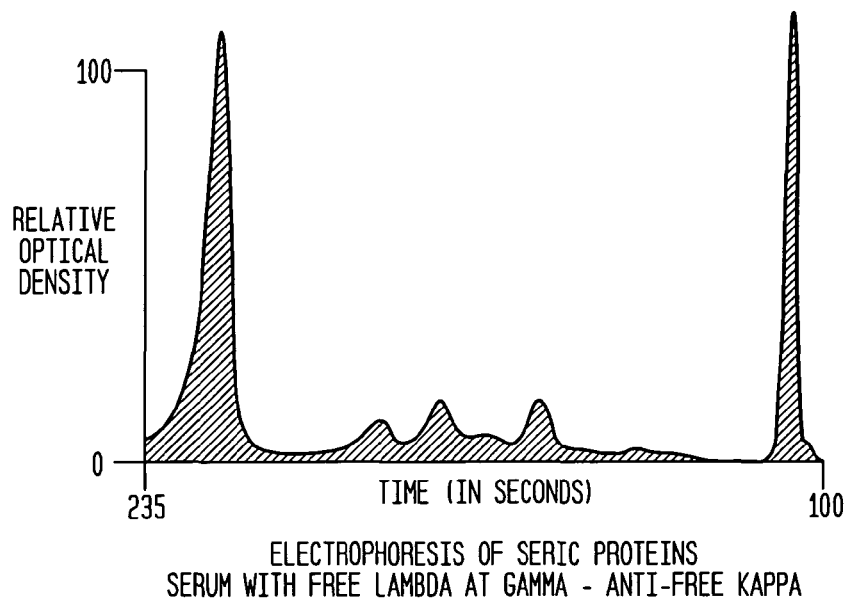
FIG. 12d is an electrophoretic profile of serum containing anti-free kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 12E:
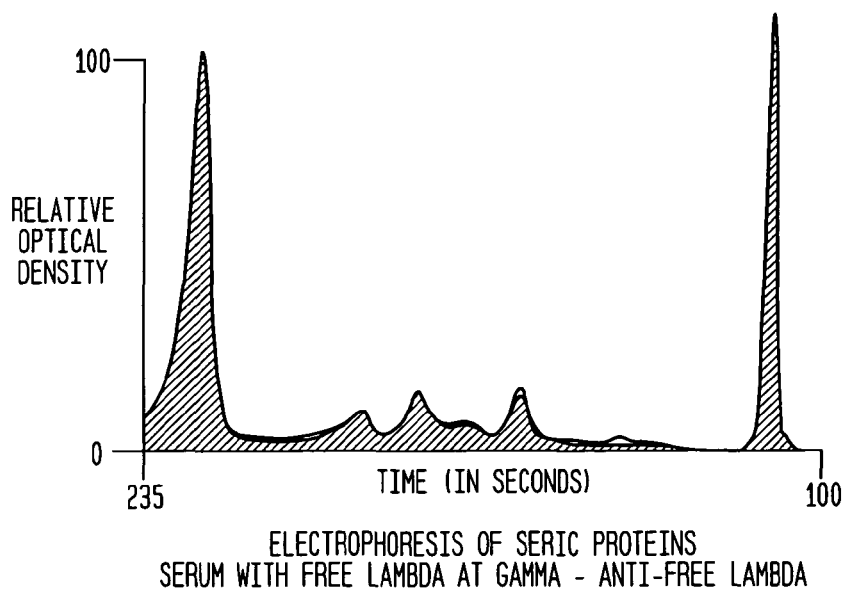
FIG. 12e is an electrophoretic profile of serum containing anti-free lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

Immunotyping of a serum containing a free lambda type Mc protein migrating to gamma on CAPILLARYS® with Sebia CAPILLARYS® B1B2+ buffer (acquisition window 100-235 s): 6 aliquots of this serum were mixed with 5 antibodies modified with 1,2,4-benzenetricarboxylic anhydride (trivalent antiserum (mixture of anti-IgG, -IgA, -IgM antibodies), anti-kappa, anti-lambda, anti-free kappa, anti-free lambda) and with the medium for these antibodies (no antibodies: ELP track). Comparison with the ELP track (in black; FIG. 12) clearly shows the disappearance of the polyclonal background but not of the Mc peak on the track treated with trivalent antiserum. In parallel, the disappearance of the Mc peak was observed on the anti-lambda and anti-free lambda tracks. On the anti-kappa and anti-free kappa tracks, only a reduction in the polyclonal background was observed. Note also the absence of beta-2 fraction for this serum and the absence of interference of the immunocomplexes and modified antibodies with the globulin migration. The peak migrating in front of the gammas is an injection marker to facilitate superimposition of the profiles.

Example 13

Figure 13:
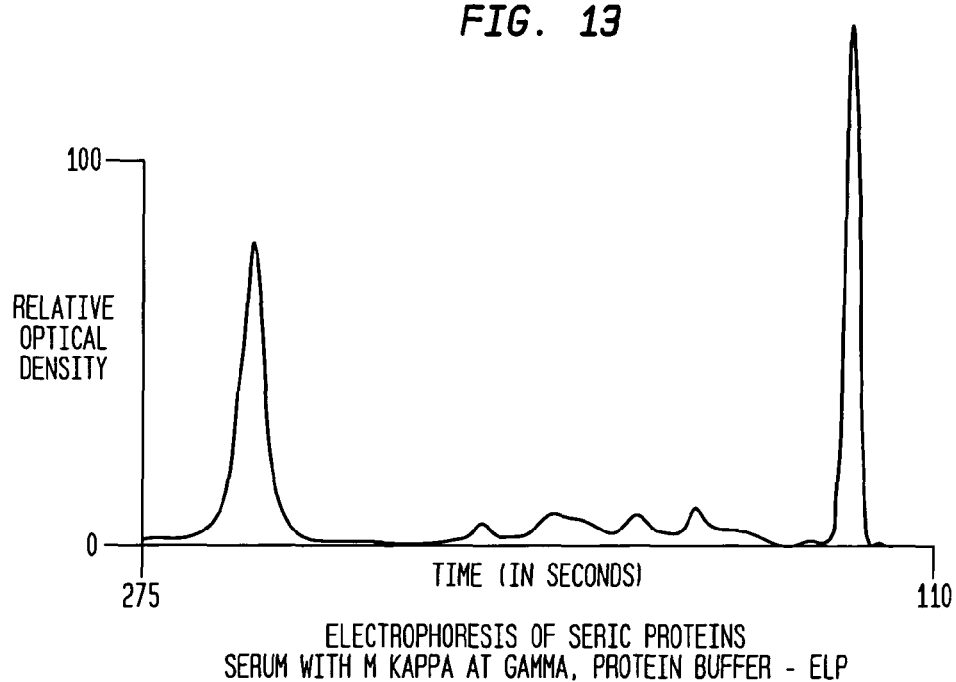
Figure 13A:
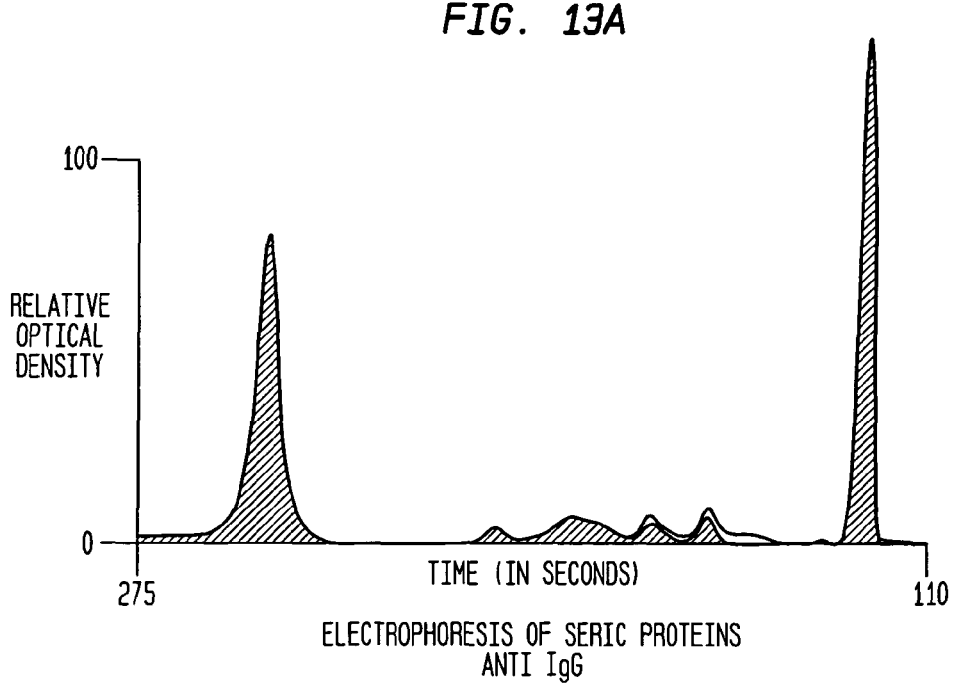
FIG. 13a is an electrophoretic profile of serum containing anti-IgG antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 13B:
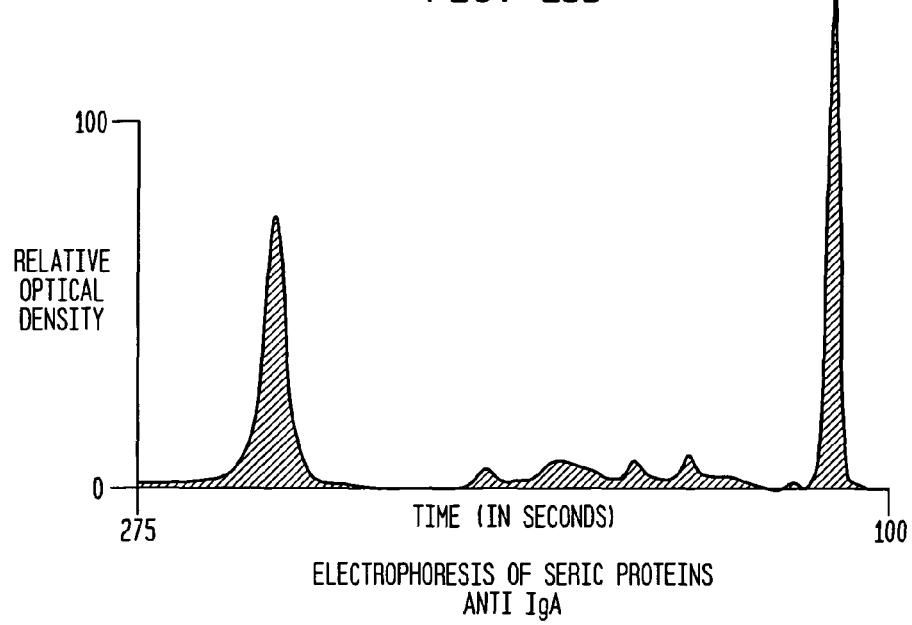
FIG. 13b is an electrophoretic profile of serum containing anti-IgA antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 13C:
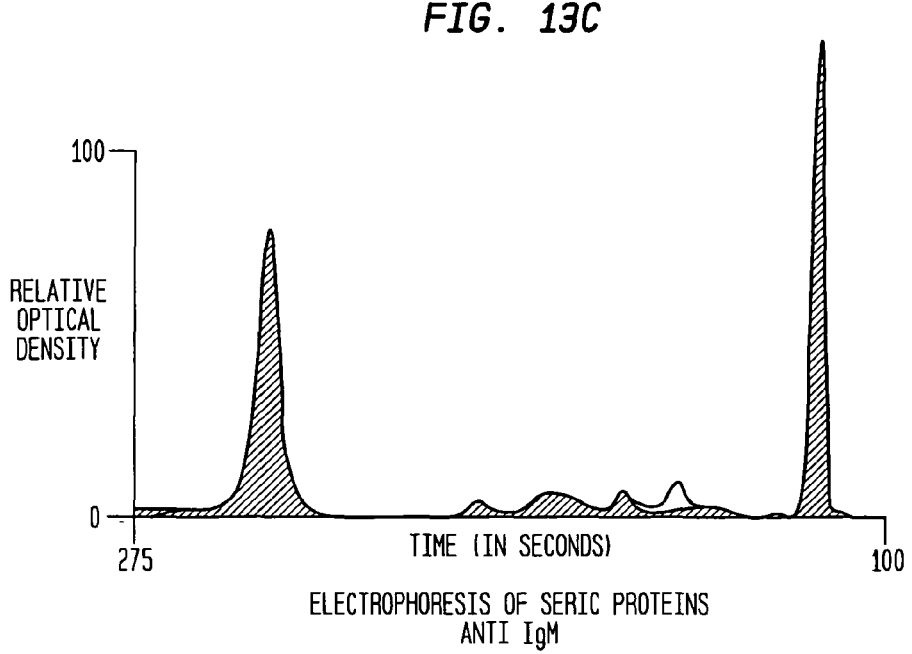
FIG. 13c is an electrophoretic profile of serum containing anti-IgM antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 13D:
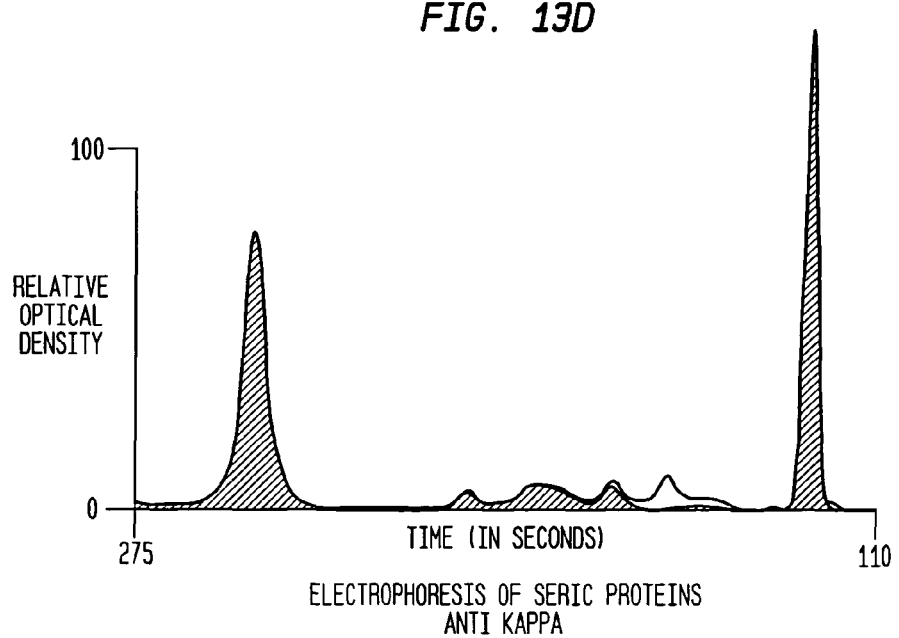
FIG. 13d is an electrophoretic profile of serum containing anti-kappa antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".
Figure 13E:
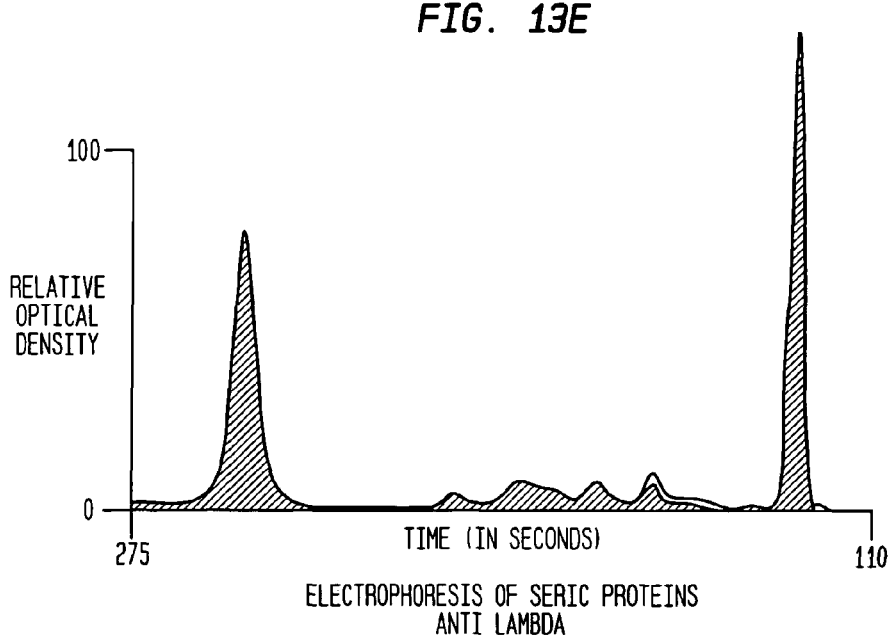
FIG. 13e is an electrophoretic profile of serum containing anti-lambda antibodies modified with 1,2,4-benzenetricarboxylic acid anhydride. The gray surface of the profile represents seric proteins separated in the presence of the antibodies of the invention. The profile of the seric proteins separated outside the presence of the antibodies also appears, but with a fainter line "(elp)".

Immunotyping of a serum containing a type M kappa Mc protein migrating to gamma on a CAPILLARYS® apparatus with CAPILLARYS® Protein(e) buffer (acquisition window 110-275 s): 6 aliquots of this serum were mixed with 5 antibodies modified with 1,2,4-benzenetricarboxylic anhydride (anti-IgG, -IgA, -IgM, -kappa, -lambda,) and with the medium for said antibodies (no antibodies: ELP track). Comparison with the ELP track (in black; FIG. 13) clearly shows the disappearance of the Mc peak at gamma on the aliquots treated with anti-IgM and anti-kappa. On the other tracks, only a reduction in the polyclonal background was observed. Note also the absence of interference of the immunocomplexes and modified antibodies with the globulin migration. The peak migrating in front of the gammas is an injection marker to facilitate superimposition of the profiles.

The invention claimed is:

1. A method for capillary electrophoresis of a biological sample, comprising employing negatively surcharged modified antibodies and applying a charge for a time sufficient to allow these modified antibodies to migrate to a zone located outside migration zones for globulins of the biological sample when said globulins are separated during electrophoresis, said antibodies having antigenic specificity for a predetermined target protein, wherein said globulins are gamma, beta-2, beta-1, alpha-2 and alpha-1 globulins, wherein said negatively charged modified antibodies are reaction products of antibodies with 1,2,4-benzenetricarboxylic anhydride.

2. The method according to claim 1, further comprising the following steps:
   a) separating constituents of a first aliquot portion of the biological sample by capillary electrophoresis, in the presence of the negatively surcharged modified antibodies having a determined antigenic specificity, the antibodies forming a complex of the antigen-antibody type with a monoclonal protein that may be present in the biological sample,
   b) detecting the separated constituents of the biological sample; and
   c) comparing an electrophoretic profile obtained in steps a) and b) with an electrophoretic profile of the constituents of a second aliquot profile from the same sample separated by capillary electrophoresis in the absence of said negatively surcharged modified antibodies.

3. The method according to claim 2, wherein said negatively surcharged modified antibodies further comprise a series of antibodies having different antigenic specificities.

4. The method according to claim 2, wherein said negatively surcharged modified antibodies further comprise a series of antibodies having different antigenic specificities, brought into contact with the first aliquot portion of the biological sample to separate the constituents of the sample by capillary electrophoresis.

5. The method according to claim 2, further comprising: prior to the steps of separating the constituents of the biological sample by electrophoresis;
   1) bringing a medium containing the negatively surcharged modified antibodies having a determined antigenic specificity into contact with the first aliquot of the biological sample under incubation conditions that allow the immunological reaction between said antibodies and a target protein specifically recognized by said antibodies and bringing the second aliquot portion of the biological sample into contact with said medium free of the negatively surcharged modified antibodies; and
   2) injecting the first aliquot of the biological sample incubated in step 1) into an electrophoresis capillary.

6. The method according to claim 3, further comprising: prior to separating the constituents of the biological sample by electrophoresis;
   1) bringing a medium containing the negatively surcharged modified antibodies having a determined antigenic specificity into contact with a first aliquot of the biological sample under incubation conditions that allow the immunological reaction between said antibodies and a target protein specifically recognized by said antibodies present in the biological sample, and bringing a second aliquot of the biological sample into contact with said medium free of modified antibodies; and
   2) injecting the first and second aliquots of the biological sample incubated in step 1) into an electrophoresis capillary.

7. The method according to claim 1, further comprising: prior to separating constituents of the biological sample by electrophoresis;
   1) injecting a medium containing negatively surcharged modified antibodies having a determined antigenic specificity into an electrophoresis capillary, and injecting said medium free of said modified antibodies into another electrophoresis capillary; and
   2) injecting the biological sample into the electrophoresis capillary treated in accordance with step 1), under conditions allowing an immunological reaction between the antibodies and a target protein.

8. The method according to claim 2, further comprising: prior to separating constituents of the biological sample by electrophoresis;
   1) injecting a medium containing negatively surcharged modified antibodies having a determined antigenic specificity into an electrophoresis capillary, and injecting said medium free of said modified antibodies into another electrophoresis capillary; and
   2) injecting the biological sample into the electrophoresis capillary treated in accordance with step 1), under conditions allowing an immunological reaction between the antibodies and a target.

9. The method according to claim 2, wherein the biological sample is divided into at least n+1 aliquot portions when series of negatively surcharged modified antibodies comprises n types of antibodies with different predetermined specificities.

10. The method according to claim 5, wherein the biological sample is divided into at least n+1 aliquot portions when series of negatively surcharged modified antibodies comprises n types of antibodies with different predetermined specificities.

11. The method according to claim 7, wherein the biological sample is divided into at least n+1 aliquot portions when series of negatively surcharged modified antibodies comprises n types of antibodies with different predetermined specificities.

12. The method according to claim 1, wherein the antibodies are selected from anti-IgG, anti-IgM, anti-kappa and anti-lambda antibodies.

13. The method according to claim 2, wherein the antibodies are selected from anti-IgG, anti-IgA, anti-IgM, anti-kappa and anti-lambda antibodies.

14. The method according to claim 1, wherein anti-IgG antibodies, anti-IgA antibodies, anti-IgM antibodies, anti-kappa antibodies and anti-lambda antibodies are employed.

15. The method according to claim 2, wherein anti-IgG antibodies, anti-IgA antibodies, anti-IgM antibodies, anti-kappa antibodies and anti-lambda antibodies are employed.

16. The method according to claim 1, wherein the negatively surcharged modified antibody is provided in excess with respect to the target protein, present in the biological sample.

17. The method according to claim 2, wherein the negatively surcharged modified antibody is provided in excess with respect to the target protein, present in the biological sample.

18. The method according to claim 1, wherein the negatively surcharged modified antibody is provided in excess with respect to the target protein, present in the biological sample.

19. The method according to claim 1, wherein said reaction comprises extemporaneous dissolution of the anhydride in dimethylformamide (DMF) and bringing the dissolved anhydride into contact with the antibodies in solution to react the anhydride and the antibodies, said reaction being carried out at 37° C. under conditions allowing the negative charges to graft to the antibodies.

20. A method for capillary electrophoresis of a biological sample, comprising employing negatively surcharged modified antibodies and applying a charge for a time sufficient to allow these modified antibodies to migrate to a zone located outside migration zones for globulins of the biological sample when said globulins are separated during electrophoresis, said antibodies having antigenic specificity for a predetermined target protein, wherein said globulins are gamma, beta-2, beta-1, alpha-2 and alpha-1 globulins, and wherein said negatively surcharged modified antibodies are reaction products of antibodies with mellitic acid.

21. The method according to claim 2, wherein said capillary electrophoresis is carried out in an alkaline buffer at a pH in the range between 9 to 11, containing a buffer compound and at least one additive that can increase the ionic strength of an analysis buffer.

22. The method according to claim 1, wherein said capillary electrophoresis is carried out in an alkaline buffer at a pH in the range between 9 to 11, containing a buffer compound and at least one additive that can increase the ionic strength of an analysis buffer.

23. The method according to claim 2, in which the biological sample is selected from samples of plasma, urine and cephalorhachidian fluid.

24. The method according to claim 2, in which the biological sample is a sample of serum.

25. The method according to claim 1, wherein monoclonal proteins (Mc proteins) are present in the biological sample.

26. The method according to claim 2, wherein monoclonal proteins (Mc proteins) are present in the biological sample.

27. The method according to claim 1, wherein monoclonal proteins (Mc proteins) are present in the biological sample.

28. A method for investigating and typing monoclonal proteins (Mc proteins) in a biological sample, comprising performing said capillary electrophoresis according to claim 2 on different aliquots of the biological sample, wherein each aliquot portion is brought into contact with said negatively surcharged modified antibodies selected from the group consisting of anti-IgG, anti-IgA, anti-IgM, anti kappa and anti-lambda immunoglobulins.

29. The method according to claim 1, wherein the anhydride is dissolved in pure dimethylformamide (DMF).

30. A method for capillary electrophoresis of a biological sample comprising: employing negatively surcharged modified antibodies and applying a charge for a time sufficient to allow these modified antibodies to migrate to a zone located outside migration zones for globulins of the biological sample when said globulins are separated during electrophoresis, said antibodies having antigenic specificity for a predetermined target protein, wherein said negatively surcharged modified antibodies are reaction products of antibodies with benzenetricarboxylic anhydride and said anhydride has at least one carboxylic acid function.

* * * * *

UNITED STATES PATENT AND TRADEMARK OFFICE
CERTIFICATE OF CORRECTION

PATENT NO. : 8,609,435 B2
APPLICATION NO. : 10/984252
DATED : December 17, 2013
INVENTOR(S) : Frédéric Robert and Régis Andre It is certified that error appears in the above-identified patent and that said Letters Patent is hereby corrected as shown below:

In the claims

Column 26

Lines 30-31, Claim 9. "portions when series" should read -- portions when a series --.

Lines 35-36, Claim 10. "portions when series" should read -- portions when a series --.

Lines 40-41, Claim 11. "portions when series" should read -- portions when a series --.

Line 45, Claim 12. "anti-IgG, anti-IgM" should read -- anti-IgG, anti-IgA, anti-IgM --.

Line 58, Claim 16. Delete the "," between "protein" and "present.".

Line 62, Claim 17. Delete the "," between "protein" and "present.".

Line 66, Claim 18. Delete the "," between "protein" and "present.".

Signed and Sealed this
Twenty-eighth Day of June, 2016

Michelle K. Lee
*Director of the United States Patent and Trademark Office*